US010292600B2

(12) United States Patent
Morikawa et al.

(10) Patent No.: US 10,292,600 B2
(45) Date of Patent: May 21, 2019

(54) BIOSIGNAL MEASUREMENT APPARATUS AND BIOSIGNAL MEASUREMENT METHOD

(71) Applicant: Panasonic Corporation, Osaka (JP)

(72) Inventors: Koji Morikawa, Kyoto (JP); Jun Ozawa, Nara (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 636 days.

(21) Appl. No.: 14/313,176

(22) Filed: Jun. 24, 2014

(65) Prior Publication Data
US 2014/0309540 A1 Oct. 16, 2014

Related U.S. Application Data

(63) Continuation of application No. PCT/JP2013/004126, filed on Jul. 3, 2013.

(30) Foreign Application Priority Data

Jul. 6, 2012 (JP) .................. 2012-153076

(51) Int. Cl.
A61B 5/00 (2006.01)
A61B 5/0205 (2006.01)
(Continued)

(52) U.S. Cl.
CPC .......... A61B 5/0205 (2013.01); A61B 5/0456 (2013.01); A61B 5/0826 (2013.01);
(Continued)

(58) Field of Classification Search
None
See application file for complete search history.

(56) References Cited

U.S. PATENT DOCUMENTS 5,794,623 A * 8/1998 Forbes ................. A61B 5/0452
128/901
5,984,954 A * 11/1999 Cohen .................. A61B 5/0456
600/521

(Continued)

FOREIGN PATENT DOCUMENTS

JP 2007-517553 7/2007
JP 2008-508907 3/2008
(Continued)

OTHER PUBLICATIONS

International Search Report dated Aug. 6, 2013 in corresponding International Application No. PCT/JP2013/004126.
(Continued)

Primary Examiner — Christian Jang
Assistant Examiner — Sarah R Kingsley
(74) Attorney, Agent, or Firm — Wenderoth, Lind & Ponack, L.L.P.

(57) ABSTRACT

A biosignal measurement apparatus includes: a potential difference measurement unit that measures a potential difference between a plurality of electrodes of an electrode unit placed on a user's chest; an ECG analysis unit that obtains an electrocardiogram (ECG) indicating a temporal variation of a cardiac potential of the user, from the potential difference measured by the potential difference measurement unit; an impedance measurement switching unit that determines a start timing of a first period which is a period not including an R wave, using the ECG obtained by the ECG analysis unit; an impedance measurement unit that measures an impedance between the plurality of electrodes in the first period; and a respiratory calculation unit that calculates respiratory information related to respiration of the user, based on a temporal variation of the impedance measured by the impedance measurement unit.

12 Claims, 18 Drawing Sheets

(51) Int. Cl.
*A61B 5/0456* (2006.01)
*A61B 5/08* (2006.01)
*A61B 5/04* (2006.01)
*A61B 5/0408* (2006.01)
*A61B 5/0468* (2006.01)

(52) U.S. Cl.
CPC ......... *A61B 5/0408* (2013.01); *A61B 5/04012* (2013.01); *A61B 5/0468* (2013.01); *A61B 5/0809* (2013.01); *A61B 5/4818* (2013.01); *A61B 5/6804* (2013.01)

(56) References Cited

U.S. PATENT DOCUMENTS

| | | | |
|---|---|---|---|
| 6,449,509 B1 * | 9/2002 | Park | A61N 1/36521 600/533 |
| 6,556,695 B1 * | 4/2003 | Packer | A61B 5/02007 382/128 |
| 6,616,608 B2 * | 9/2003 | Honda | A61B 5/0205 600/301 |
| 2007/0032733 A1 | 2/2007 | Burton | |
| 2007/0239781 A1 * | 10/2007 | Kraft | G11B 27/102 |
| 2007/0293781 A1 * | 12/2007 | Sims | A61B 5/1135 600/534 |
| 2008/0306559 A1 | 12/2008 | Allen et al. | |
| 2009/0012408 A1 | 1/2009 | Nagata et al. | |
| 2010/0217133 A1 * | 8/2010 | Nilsen | A61B 5/0205 600/484 |
| 2010/0324434 A1 * | 12/2010 | Allmendinger | A61B 5/0456 600/509 |
| 2011/0066062 A1 * | 3/2011 | Banet | A61B 5/0402 600/534 |
| 2014/0309540 A1 * | 10/2014 | Morikawa | A61B 5/0456 600/484 |

FOREIGN PATENT DOCUMENTS

| | | |
|---|---|---|
| JP | 2010-94236 | 4/2010 |
| JP | 2010-540124 | 12/2010 |
| JP | 2011-172964 | 9/2011 |
| JP | 4788915 | 10/2011 |
| JP | 4852698 | 1/2012 |
| JP | 2012-95905 | 5/2012 |
| WO | 2005/067790 | 7/2005 |
| WO | 2005/089642 | 9/2005 |
| WO | 2006/005557 | 1/2006 |
| WO | 2009/043087 | 4/2009 |

OTHER PUBLICATIONS

Yoshifumi Yasuda et.al., "Modified thoracic impedance plethysmography to monitor sleep apnea syndromes", Sleep Medicine, vol. 6, pp. 215-224, May 2005.

Akihito Umezu et al., "Kyobu Impedance hou ni yoru suiminji no kokyu no keisoku to sono mondaiten (Measurement of respiration during sleep by thoracic impedance method and its problems)", The 18th Annual Scientific Meeting of Respiratory and Exercise Physiology Proceedings, pp. 13-16, Sep. 2004 (with English translation).

* cited by examiner

BIOSIGNAL MEASUREMENT APPARATUS AND BIOSIGNAL MEASUREMENT METHOD

CROSS-REFERENCE TO RELATED APPLICATIONS

This is a continuation application of PCT International Application No. PCT/JP2013/004126 filed on Jul. 3, 2013, designating the United States of America, which is based on and claims priority of Japanese Patent Application No. 2012-153076 filed on Jul. 6, 2012. The entire disclosures of the above-identified applications, including the specifications, drawings and claims are incorporated herein by reference in their entirety.

FIELD

One or more exemplary embodiments disclosed herein relate generally to a biosignal measurement apparatus and a biosignal measurement method.

BACKGROUND

As means to electrically and mechanically measure a user's body condition, a method of measuring and recording a measurement object for a long time is increasingly used in recent years. Examples of basic electrical information indicating the user's body condition include an electroencephalogram (EEG) relating to the brain and an electrocardiogram (ECG) relating to the motion of the heart.

Techniques for easily obtaining an ECG and respiratory information are disclosed (for example, Patent Literatures (PTLs) and 2). PTL 1 discloses a method in which electrodes for ECG measurement and electrodes for respiratory value measurement are separately placed inside a garment and an ECG and respiration are simultaneously measured from potential changes between the electrodes. PTL 2 discloses a method in which information related to respiratory intervals is calculated by analyzing heartbeat variation data obtained from a cardiac potential.

CITATION LIST

Patent Literature

[PTL 1]
Japanese Patent Publication No. 4788915
[PTL 2]
Japanese Patent Publication No. 4852698

Non Patent Literature

[NPL 1]
Yoshifumi Yasuda et al., "Modified thoracic impedance plethysmography to monitor sleep apnea syndromes", Sleep Medicine, Vol. 6, pp. 215-224 (2005)
[NPL 2]
Akihito Umezu and Yoshifumi Yasuda, Toyohashi University of Technology, "Kyobu impedance hou ni yoru suiminji no kokyu no keisoku to sono mondaiten (Measurement of respiration during sleep by thoracic impedance method and its problems)", The 18th Annual Scientific Meeting of Respiratory and Exercise Physiology Proceedings, pp. 13-16, September 2004

SUMMARY

Technical Problem

However, the following problem exists: respiratory information and heartbeat information cannot be simultaneously obtained using electrodes placed on the chest.

One non-limiting and exemplary embodiment provides a biosignal measurement apparatus and the like that can simultaneously obtain respiratory information and heartbeat information using the same electrodes.

Solution to Problem

In one general aspect, the techniques disclosed here feature a biosignal measurement apparatus including: a potential difference measurement unit that measures a potential difference between a plurality of electrodes placed on a user's chest; an ECG obtainment unit that obtains an electrocardiogram (ECG) indicating a temporal variation of a cardiac potential of the user, from the potential difference measured by the potential difference measurement unit; an impedance measurement switching unit that determines a start timing of a first period which is a period not including an R wave, in a waveform of the ECG obtained by the ECG obtainment unit; an impedance measurement unit that measures an impedance between the plurality of electrodes in the first period; and a respiratory calculation unit that calculates respiratory information related to respiration of the user, based on a temporal variation of the impedance measured by the impedance measurement unit.

General and specific aspect(s) disclosed above may be implemented using a system, a method, an integrated circuit, a computer program, or a computer-readable recording medium such as a CD-ROM, or any combination of systems, methods, integrated circuits, computer programs, or computer-readable recording media.

Additional benefits and advantages of the disclosed embodiments will be apparent from the Specification and Drawings. The benefits and/or advantages may be individually obtained by the various embodiments and features of the Specification and Drawings, which need not all be provided in order to obtain one or more of such benefits and/or advantages.

Advantageous Effects

A biosignal measurement apparatus according to one or more exemplary embodiments or features disclosed herein can simultaneously measure heartbeat information and respiratory information using the same electrodes.

BRIEF DESCRIPTION OF DRAWINGS

These and other advantages and features will become apparent from the following description thereof taken in conjunction with the accompanying Drawings, by way of non-limiting examples of embodiments disclosed herein.

DESCRIPTION OF EMBODIMENT(S)

Figure 1:
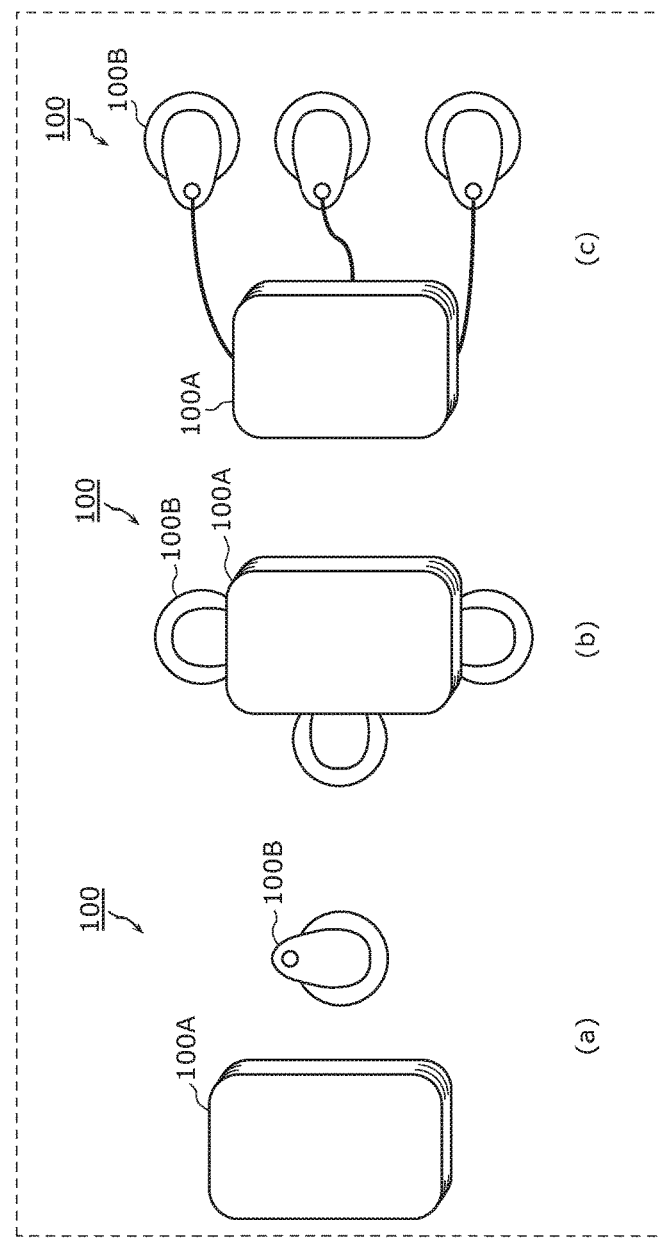
FIG. 1 is an appearance diagram of a biosignal measurement system according to Embodiment 1.

(Underlying Knowledge Forming Basis of the Present Disclosure)

In relation to the techniques for obtaining an ECG and respiratory information disclosed in the Background section, the inventors have found the following problem.

An ECG is obtained as basic biological information (vital sign) in a hospital. There is also a method of obtaining and recording an ECG for a long time (for example, 24 hours) using a portable ECG monitor called "Holter monitor", for a user suspected of having heart disease. Holter monitors are increasingly reduced in size in recent years, enabling easier measurement.

In a Holter ECG test capable of recording an ECG for a long time, symptoms such as arrhythmias undetectable in a short-time test in a hospital can be recorded. Not only an ECG but also other test items are revealed through long-time tests. For example, sleep apnea syndrome which is a respiratory disease closely associated with arrhythmias cannot be evaluated with an ECG alone, as information related to respiration is also necessary. For testing for sleep apnea syndrome, overnight polysomnography that simultaneously measures an ECG, respiration, and an EEG is currently required. This test needs to be performed with the patient staying overnight in the hospital. Overnight polysomnography is burdensome to both the hospital and the patient. It is not practical to perform such a burdensome test in a stage where the disease is merely suspected.

Obtaining respiratory disease-related information and in particular respiratory rate-related information with the same ease as the Holter monitor is likely to contribute to early disease detection and diagnosis.

Conventionally, a pulse oximeter is mainly used in order to easily measure respiration. The pulse oximeter is an instrument for measuring arterial oxygen saturation. The pulse oximeter measures arterial oxygen saturation with a sensor called "probe" attached to the subject's fingertip. The sensor includes a red light emitting diode (LED). By measuring light transmitted through the finger (light of the red LED transmitted through the finger), oxygen content in arterial blood in the finger can be measured in real time. Hence, in the case where both an ECG and respiratory information are required, it is necessary to attach the electrodes for the ECG monitor to the chest and also attach the probe of the pulse oximeter to the fingertip.

In view of this, techniques for easily obtaining an ECG and respiratory information are disclosed (for example, PTLs 1 and 2). PTL 1 discloses a method in which electrodes for ECG measurement and electrodes for respiratory value measurement are separately placed inside a garment and an ECG and respiration are simultaneously measured from potential changes between the electrodes. PTL 2 discloses a method in which information related to respiratory intervals is calculated by analyzing heartbeat variation data obtained from a cardiac potential.

However, the conventional methods of obtaining both heartbeat information and respiratory information have the following problem.

In the technique disclosed in PTL 1, there is a problem of needing to prepare a specific garment inside which the electrodes for ECG measurement are placed. There is also a problem of failing to appropriately bring the electrodes into contact with the body surface if the garment does not fit the subject's physical constitution, which results in a measurement error.

The technique disclosed in PTL 2 is based on an assumption that the variation cycle of the heartbeat variation data corresponds to the respiratory cycle. This assumption is, however, applicable only during rest. The heart rate changes not only with the respiratory cycle but also with other factors such as a psychogenic fluctuation component and body movement and, if these factors are not negligible, the respiratory cycle may not be accurately estimated. In other words, there is a problem of being unable to accurately estimate the respiratory cycle in the case where the heartbeat variation cycle does not correspond to the respiratory cycle.

Thus, the following problem exists: respiratory information and heartbeat information cannot be simultaneously obtained using electrodes placed on the chest.

The inventors have focused attention on a thoracic impedance method (for example, Non Patent Literature (NPL) 1) for electrically measuring respiration. NPL 1 proposes a technique of obtaining respiratory information by measuring changes in thoracic impedance. The thoracic impedance includes a component that changes as the volume of the lungs changes according to respiration. Therefore, information related to respiration can be obtained more directly from the thoracic impedance. For example, it is possible to associate the amount of change of impedance with the respiratory depth.

One non-limiting and exemplary embodiment provides a biosignal measurement apparatus and the like that can simultaneously obtain respiratory information and heartbeat information.

According to an exemplary embodiment disclosed herein, a biosignal measurement apparatus includes: a potential difference measurement unit that measures a potential difference between a plurality of electrodes placed on a user's chest; an ECG obtainment unit that obtains an electrocardiogram (ECG) indicating a temporal variation of a cardiac potential of the user, from the potential difference measured by the potential difference measurement unit; an impedance measurement switching unit that determines a start timing of a first period which is a period not including an R wave, in a waveform of the ECG obtained by the ECG obtainment unit; an impedance measurement unit that measures an impedance between the plurality of electrodes in the first period; and a respiratory calculation unit that calculates respiratory information related to respiration of the user, based on a temporal variation of the impedance measured by the impedance measurement unit.

With this, the biosignal measurement apparatus can successively obtain heartbeat information by ECG measurement and respiratory information by impedance measurement in a time division manner using the same electrodes. Here, respiration is measured in the period not including the R wave which is a characteristic waveform in the ECG. Thus, measurement data for the period that includes information necessary for obtainment of heartbeat information is obtained in the ECG measurement period, and measurement data other than the above-mentioned measurement data is obtained in the impedance measurement period. Respiratory information and heartbeat information can be simultaneously obtained in this way.

For example, the ECG obtainment unit may obtain the ECG of the user, from the potential difference measured by the potential difference measurement unit in a second period which is a period including the R wave in the ECG and different from the first period.

With this, the R wave which is a characteristic waveform in the ECG can be included in the ECG measurement result. By detecting the R wave in the ECG measurement result, it is possible to obtain heartbeat-related information such as a heart rate and a heartbeat depth. This enables more accurate heart rate measurement.

For example, the ECG obtainment unit may further calculate a heart rate based on a time interval between two adjacent R waves in the ECG, and output the calculated heart rate.

With this, the heart rate can be calculated based on the time interval between the R waves included in the ECG measurement result. This enables more accurate heart rate measurement.

For example, the impedance measurement switching unit may determine the start timing of the first period to be when a predetermined time elapses based on the R wave in the ECG obtained by the ECG obtainment unit.

For example, the impedance measurement switching unit may determine the start timing of the first period to be when a predetermined time elapses from a most recent time at which the R wave appears in the ECG.

With this, the start timing of the period for respiratory measurement can be determined based on the R wave included in the ECG measurement result. Since the heartbeat cycle changes from moment to moment, it is impossible to set the period for respiratory measurement in a predetermined constant cycle. Accordingly, the start timing of the period for respiratory measurement is set based on the time of the R wave in a period of one heartbeat. Thus, the period for respiratory measurement can be set in the period not including the R wave, in each heartbeat period.

For example, the ECG obtainment unit may obtain the ECG including a part in which the first period and the second period alternate, and the respiratory calculation unit may: obtain the temporal variation of the impedance between the plurality of electrodes, by temporally interpolating the impedance in the second period between the impedance measured in the first period preceding the second period and the impedance measured in the first period following the second period; and calculate the respiratory information based on a peak of a low frequency component of the obtained temporal variation of the impedance.

With this, a continuous impedance measurement result can be obtained by temporally interpolating impedance measurement results in a plurality of separate periods. Information related to respiration can then be obtained from the impedance measurement result.

For example, the impedance measurement switching unit may further determine a length of the first period, based on a time interval between two adjacent R waves in the ECG obtained by the ECG obtainment unit.

For example, the impedance measurement switching unit may receive a first time at which the R wave is detected most recently, and determine the length of the first period to cause the first period to be included between the first time and a time at which the time interval between the two adjacent R waves elapses from the first time.

With this, the length of the period for respiratory measurement can be determined based on the time interval between the R waves included in the ECG measurement result. Since the heartbeat cycle changes from moment to moment, it is impossible to set the period for respiratory measurement in a predetermined constant cycle. Accordingly, the length of the period for respiratory measurement is set based on the time of the R wave in a period of one heartbeat. Thus, the period for respiratory measurement can be set in the period not including the R wave, in each heartbeat period.

For example, the biosignal measurement apparatus may further include a current application unit that starts applying a current between the plurality of electrodes, at the start timing determined by the impedance measurement switching unit, wherein the impedance measurement unit measures the impedance between the plurality of electrodes in the first period, based on the potential difference between the plurality of electrodes and a magnitude of the current applied by the current application unit.

With this, the electrodes used for measuring the potential difference can also be used for measuring the impedance. Impedance measurement can be performed with no need to use new electrodes in addition to the electrodes used when performing ECG measurement. Respiratory information and heartbeat information can be simultaneously obtained in this way.

For example, the respiratory calculation unit may: calculate a plurality of respiratory information candidates by performing the temporal interpolation according to a plurality of different methods; select, from the plurality of respiratory information candidates, a respiratory information candidate indicating a higher respiratory rate when a heart rate calculated by the ECG obtainment unit is higher; and output the selected respiratory information candidate as the respiratory information.

With this, respiratory information that is assumed to be correct can be selected from the plurality of estimated respiratory rate candidates, through the use of the correlation between the heart rate and the respiratory rate. This enables more accurate respiratory rate measurement.

For example, the respiratory calculation unit may: calculate a plurality of respiratory information candidates by performing the temporal interpolation according to a plurality of different methods; select, from the plurality of respiratory information candidates, a respiratory information candidate indicating a lower respiratory rate when an amplitude of the temporal variation of the impedance measured by the impedance measurement unit is higher; and output the selected respiratory information candidate as the respiratory information.

With this, respiratory information that is assumed to be correct can be selected from the plurality of estimated respiratory rate candidates, through the use of the correlation between the heart rate and the respiratory depth. This enables more accurate respiratory rate measurement.

For example, the impedance measurement switching unit may further determine a start timing and a length of a preliminary measurement period which is a period for continuously measuring the cardiac potential of the user, the ECG obtainment unit may obtain the temporal variation of the cardiac potential of the user in the preliminary measurement period, from the potential difference measured by the potential difference measurement unit in the preliminary measurement period, and the impedance measurement switching unit may determine the start timing and a length of the first period, based on the temporal variation of the cardiac potential of the user in the preliminary measurement period.

With this, in the case where an abnormality or the like is detected based on the ECG continuously measured in the preliminary period, the start timing and the length of the period for respiratory measurement can be adjusted so that the abnormality is not included in the period for respiratory measurement, i.e. the abnormality is included in the ECG.

For example, the ECG obtainment unit may further detect an abnormality of a P wave or an ST wave, based on the obtained temporal variation of the cardiac potential of the user in the preliminary measurement period, and the impedance measurement switching unit may determine the start timing and the length of the first period, to cause the P wave or the ST wave having the abnormality detected by the ECG obtainment unit and the R wave to be included in the second period.

With this, in the case where an abnormality is detected in the P wave or the ST wave in the ECG continuously measured in the preliminary period, the start timing and the length of the period for respiratory measurement can be adjusted so that the P wave or the ST wave having the abnormality is not included in the period for respiratory measurement, i.e. the P wave or the ST wave is included in the ECG together with the R wave.

These general and specific aspects may be implemented using a system, a method, an integrated circuit, a computer program, or a computer-readable recording medium such as a CD-ROM, or any combination of systems, methods, integrated circuits, computer programs, or computer-readable recording media.

Hereinafter, certain exemplary embodiments are described in greater detail with reference to the accompanying Drawings.

Each of the exemplary embodiments described below shows a general or specific example. The numerical values, shapes, materials, structural elements, the arrangement and connection of the structural elements, steps, the processing order of the steps etc. shown in the following exemplary embodiments are mere examples, and therefore do not limit the scope of the appended Claims and their equivalents. Therefore, among the structural elements in the following exemplary embodiments, structural elements not recited in any one of the independent claims are described as arbitrary structural elements.

Embodiment 1

This embodiment describes an example of placing a plurality of electrodes on the chest of a user (subject) and simultaneously measuring heartbeat information and respiratory information using the plurality of electrodes. The term "heartbeat information" means information related to the user's heartbeat. Specific examples of the heartbeat information include a heart rate and an ECG waveform. The term "respiratory information" means information related to the user's respiration. Specific examples of the respiratory information include a respiratory rate, a respiratory depth, and whether or not respiration is suspended.

FIG. 1 is an appearance diagram of a biosignal measurement system 100 according to Embodiment 1. The biosignal measurement system 100 according to Embodiment 1 includes a biosignal measurement apparatus (not shown). An embodiment of the biosignal measurement apparatus is described below, with reference to FIG. 1.

As shown in (a) in FIG. 1, the biosignal measurement system 100 includes a measurement subsystem 100A and an electrode unit 100B.

The measurement subsystem 100A obtains respiratory information and heartbeat information, based on a biopotential measured using the electrode unit 100B.

The electrode unit 100B includes at least two electrodes. A necessary number of electrodes for biopotential measurement are provided in the electrode unit 100B. For example, the electrode unit 100B may include two electrodes in order to measure a potential between two points. Alternatively, the electrode unit 100E may include three electrodes that are a measurement electrode, an earth electrode, and a reference electrode. The electrode unit 100B is composed of a conductive material with a predetermined size or more. Examples of the material of the electrode unit 100B include medical metal electrodes and disposable electrodes.

The electrodes included in the electrode unit 100B are placed in direct contact with the user's chest. The electrode unit 100B and the measurement subsystem 100A are electrically connected to each other. It is desirable that the electrical resistance between the electrode unit 100B and the measurement subsystem 100A is low.

For example, the electrode unit 100B may be composed of medical disposable electrodes as shown in (b) in FIG. 1, in this case, if the electrodes are hook-type electrodes, the electrode unit 100B is connected to the measurement subsystem 100A by the hooks.

In the case where a certain distance is needed between the electrodes, for instance, the electrode unit 100B may be connected to the measurement subsystem 100A via cables as shown in (c) in FIG. 1. The disposable electrodes are each composed of an electrode part and a bonding part made of an adhesive, and fixed to the body by the bond strength of the bonding part.

Figure 2:
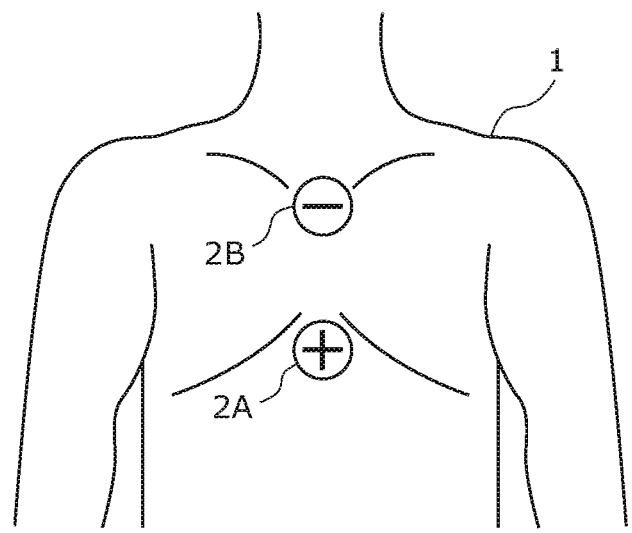
FIG. 2 is a diagram showing an example of position at which electrodes are placed.

FIG. 2 is a diagram showing an example of position at which electrodes are placed. An example of the electrode attachment position is described below, with reference to FIG. 2.

The electrode position shown in FIG. 2 is called "NASA lead". For example, an anode is placed at the lower end of the sternum of a user 1, and a cathode is placed at the upper end of the sternum of the user 1. The lead by this electrode position defines P waves well, and so has features of being suitable for analysis of arrhythmias and having little mixture of electromyogram or baseline fluctuation caused by body movement. The lead by this electrode position also has a feature of being suitable for impedance measurement by the thoracic impedance method, as described later.

Though the electrode unit 100B having two electrodes is described with reference to FIGS. 1 and 2, an electrode unit having four electrodes may be used. In this case, a current is applied between two of the four electrodes, and a voltage between the other two electrodes is measured. This enables a voltage or impedance between two electrodes to be measured more accurately than in the electrode unit having two electrodes.

Figure 3:
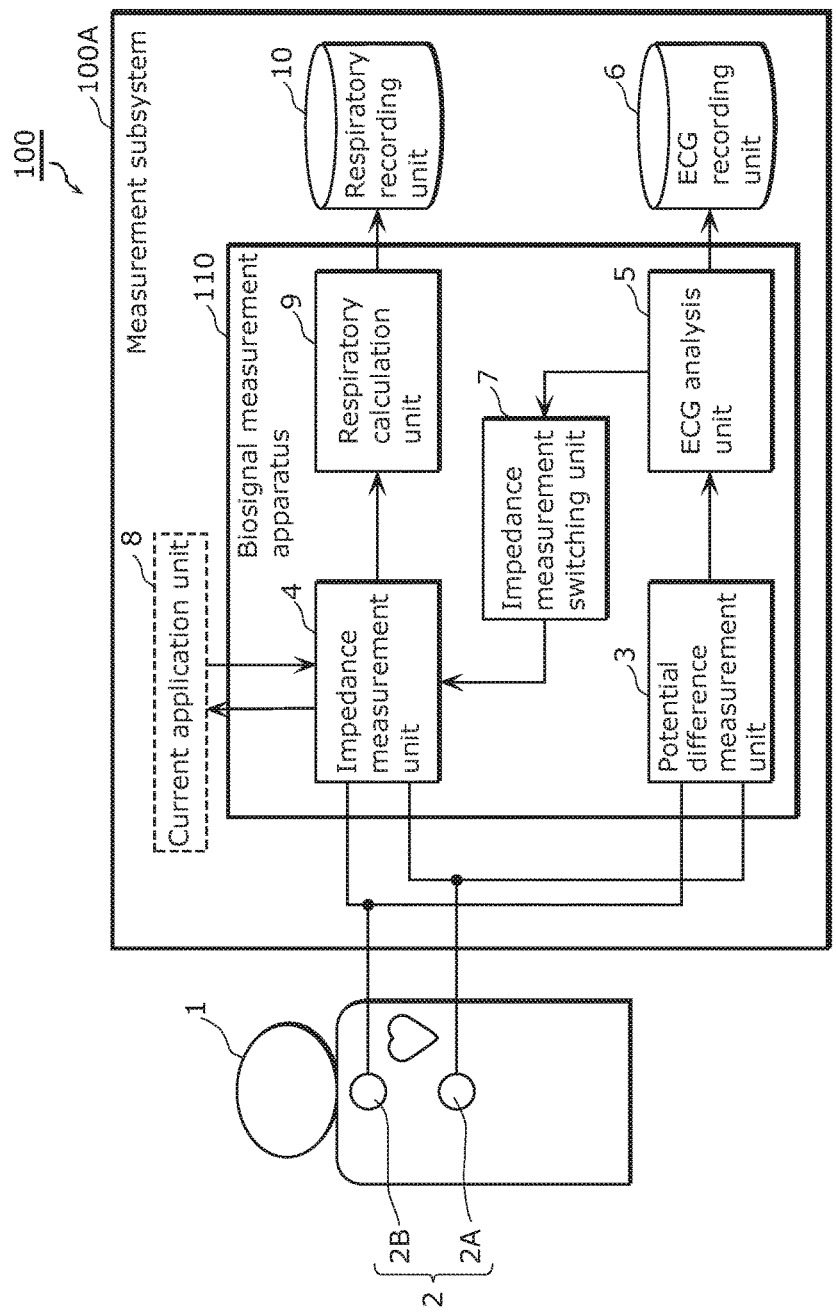
FIG. 3 is a diagram showing an example of a functional structure of the biosignal measurement system according to Embodiment 1.

FIG. 3 is a diagram showing an example of a functional structure of the biosignal measurement system 100 according to Embodiment 1. The biosignal measurement system 100 shown in FIG. 3 includes an electrode 2A, an electrode 2B, a potential difference measurement unit 3, an impedance measurement unit 4, an ECG analysis unit 5, an ECG recording unit 6, an impedance measurement switching unit 7, a current application unit 8, a respiratory calculation unit 9, and a respiratory recording unit 10.

A part having predetermined functions out of the functions of the biosignal measurement system 100 corresponds to the biosignal measurement apparatus.

A biosignal measurement apparatus 110 in the biosignal measurement system 100 shown in FIG. 3 includes the potential difference measurement unit 3, the impedance measurement unit 4, the ECG analysis unit 5, the impedance measurement switching unit 7, and the respiratory calculation unit 9. The biosignal measurement apparatus 110 is wiredly or wirelessly connected to the electrodes 2A and 2B, the ECG recording unit 6, the current application unit 8, and the respiratory recording unit 10, and is capable of transmitting and receiving information.

The electrodes 2A and 2B are placed on the chest of the user 1. The potential or impedance between these two electrodes is measured. The electrodes 2A and 2B are connected to the potential difference measurement unit 3 and the impedance measurement unit 4. The electrodes 2A and 2B are also collectively referred to as "electrode unit 2". The electrode unit 2 may include at least two electrodes.

The potential difference measurement unit 3 measures the potential difference between the electrodes 2A and 2B placed on the user's chest.

The ECG analysis unit 5 analyzes the potential difference measured by the potential difference measurement unit 3. The ECG analysis unit 5 obtains the analysis result as heartbeat data and ECG data, and records the analysis result in the ECG recording unit 6. The ECG analysis unit 5 also passes the analysis result to the impedance measurement switching unit 7. The ECG analysis unit 5 corresponds to the ECG obtainment unit. The ECG obtainment unit at least obtains information related to a temporal variation of a cardiac potential, from the potential difference measured by the potential difference measurement unit 3.

The impedance measurement switching unit 7 determines the timing of impedance measurement.

The impedance measurement unit 4 measures the impedance between the electrodes 2A and 2B.

The current application unit 8 applies a current necessary for the impedance measurement unit 4 to measure the impedance, via the electrodes 2A and 2B. Alternatively, the current application unit 8 may apply the current via electrodes 2C and 2D (not shown) for current application which are additionally attached to the body, while the electrodes 2A and 2B are used as electrodes specifically for potential difference or impedance measurement. In the case of using the electrodes 2C and 2D, the electrodes 2C and 2D are desirably positioned outside the line segment connecting the electrodes 2A and 2B. The current application unit 8 need not necessarily be provided as an independent function, and may be realized as a function of the impedance measurement unit 4.

The respiratory calculation unit 9 analyzes the impedance measured by the impedance measurement unit 4, detects the user's respiration based on the temporal variation of the impedance, and records the detection result in the respiratory recording unit 10.

Figure 4:
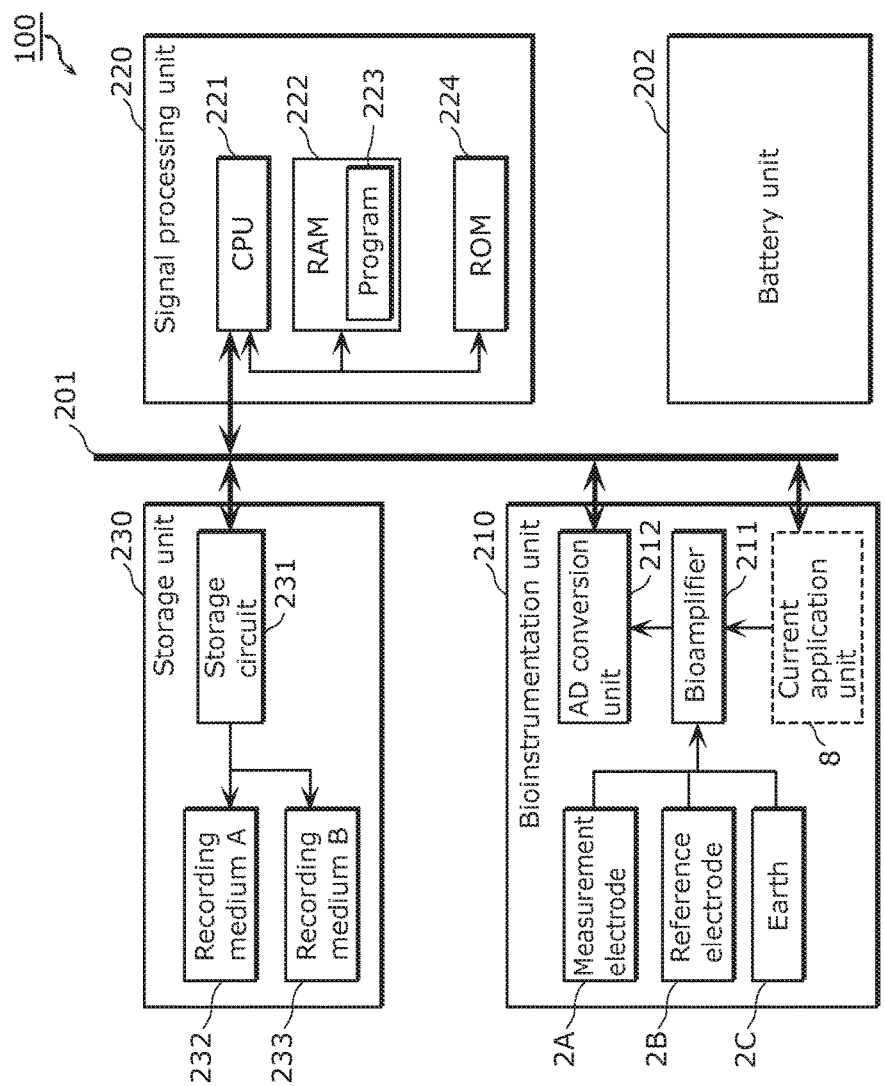
FIG. 4 is a diagram showing an example of a hardware structure of the biosignal measurement system according to Embodiment 1.

FIG. 4 is a diagram showing an example of a hardware structure of the biosignal measurement system 100 according to Embodiment 1. The biosignal measurement system 100 includes a bioinstrumentation unit 210, a signal processing unit 220, a storage unit 230, a bus 201, and a battery unit 202.

The bioinstrumentation unit 210 obtains information from a biosignal.

The signal processing unit 220 analyzes the biosignal obtained by the bioinstrumentation unit 210.

The storage unit 230 stores measurement data and processing results.

The bus 201 is a bus for connection between the bioinstrumentation unit 210, the signal processing unit 220, and the storage unit 230. The bioinstrumentation unit 210, the signal processing unit 220, and the storage unit 230 are capable of transmitting and receiving data with each other via the bus 201.

The battery unit 202 supplies power to the bioinstrumentation unit 210, the signal processing unit 220, and the storage unit 230.

The bioinstrumentation unit 210 includes the measurement electrode 2A, the reference electrode 2B, an earth 2C, a bioamplifier 211, and an AD conversion unit 212. The bioinstrumentation unit 210 may further include the current application unit 8.

The bioamplifier 211 measures the potential difference or the impedance between the measurement electrode 2A and the reference electrode 2B. For example, the impedance is measured as follows: the potential difference between the measurement electrode 2A and the reference electrode 2B is measured while applying an extremely weak current between the measurement electrode 2A and the reference electrode 2B by the current application unit 8, and the impedance is measured from the magnitude of the current and the potential difference. Switching between potential measurement and impedance measurement is controlled by the signal processing unit 220. The AD conversion unit 212 converts the data measured by the bioamplifier 211 from an analog signal to a digital signal, and sends the converted data to a CPU 221 in the signal processing unit 220 via the bus 201.

The signal processing unit 220 includes the CPU 221, a RAM 222, a program 223 stored in the RAM 222, and a ROM 224. The program 223 is stored in the RAM 222 or the ROM 224. The CPU 221 executes the program 223 stored in the RAM 222 or the ROM 224. Procedures shown in the below-mentioned flowcharts are written in the program 223. The biosignal measurement system 100 analyzes the signal of the bioinstrumentation unit 210 and stores the measurement data and analysis results in the storage unit 230, according to the program 223.

The storage unit 230 includes a storage circuit 231, a recording medium A 232, and a recording medium B 233.

The storage unit 230 records data received from the signal processing unit 220, in the recording medium A 232 or the recording medium B 233 via the storage circuit 231. The ECG recording unit 6 and the respiratory recording unit 10 in FIG. 3 are realized by the recording medium A 232 and the recording medium B 233. As an example, the ECG recording unit 6 in FIG. 3 is realized by the recording medium A 232, and records the potential data of the ECG. The respiratory recording unit 10 in FIG. 3 is realized by the recording medium B 233, and records the respiratory rate and the like which are the result of analyzing the impedance data. Though two recording media are shown as the recording medium A 232 and the recording medium B 233 in FIG. 4, the recording medium A 232 and the recording medium B 233 may be two different areas in the same recording medium.

Figure 5:
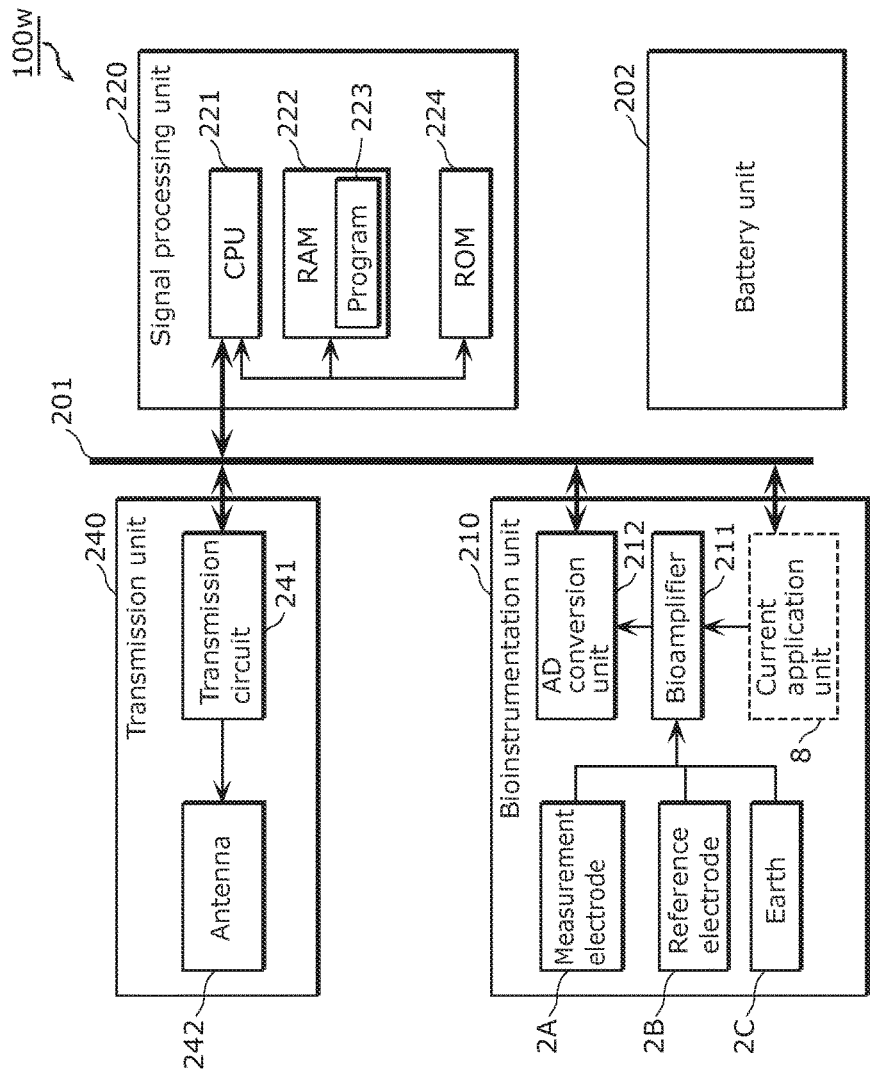
FIG. 5 is a diagram showing another example of the hardware structure of the biosignal measurement system according to Embodiment 1.

FIG. 5 is a diagram showing another example (a biosignal measurement system 100w) of the hardware structure of the biosignal measurement system 100 according to Embodiment 1. The biosignal measurement system 100w is an exemplary structure in the case where data measured by the bioinstrumentation unit 210 is transmitted to a PC, a smartphone, or the like by communication.

The biosignal measurement system 100w includes the bioinstrumentation unit 210, the signal processing unit 220, a transmission unit 240, the bus 201, and the battery unit 202. The bioinstrumentation unit 210 and the signal processing unit 220 are the same as the bioinstrumentation unit 210 and the signal processing unit 220 in the biosignal measurement system 100 in FIG. 4, and so their description is omitted.

The transmission unit 240 includes a transmission circuit 241 and an antenna 242. The transmission circuit 241 converts the measurement data or measurement result analyzed by the signal processing unit 220 into a data format suitable for a transmission protocol, and wirelessly transmits the data from the antenna 242. The data transmitted from the antenna 242 is received by a reception apparatus included in the PC, the smartphone, or the like, and used in subsequent processing.

The following describes data processing. Of the data processing, the thoracic impedance method used for measuring the respiratory rate in this embodiment is described first. The thoracic impedance method is a method of obtaining information related to the heart or the lungs from thoracic impedance. In particular, a method of obtaining information related to respiration is described based on NPLs 1 and 2 below.

Figure 6:
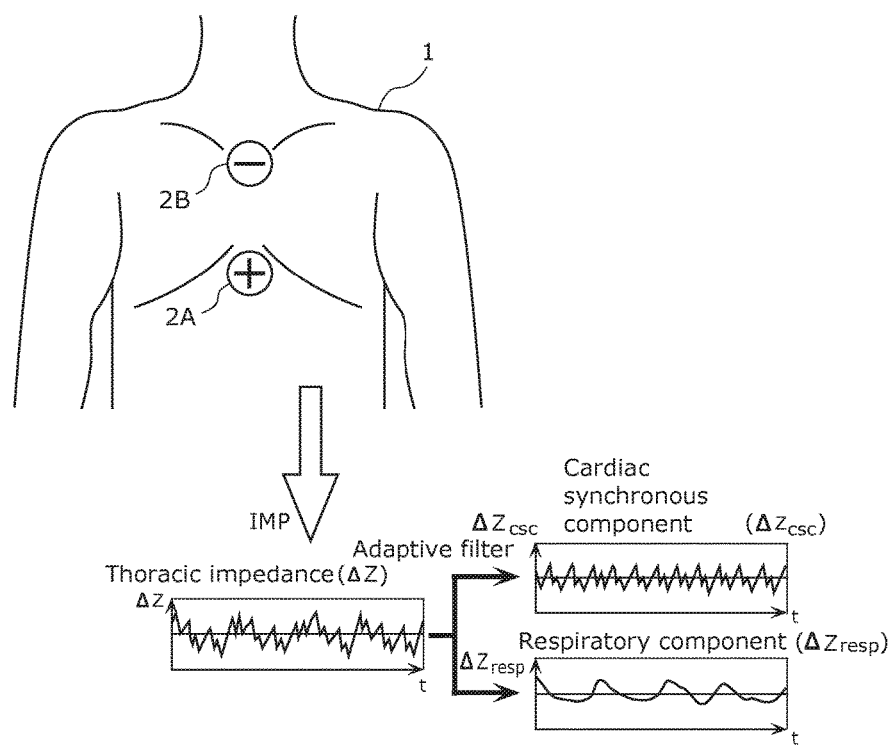
FIG. 6 is an explanatory diagram of a thoracic impedance method.

FIG. 6 is an explanatory diagram of the thoracic impedance method. As electrodes for impedance measurement, for example, an anode is placed at the lower end of the sternum of the user 1, and a cathode is placed at the upper end of the sternum of the user 1. The impedance between the electrodes is measured while applying an extremely weak current between the electrodes. The impedance data measured by this method is a signal called "thoracic impedance". The thoracic impedance includes not only a respiratory component but also a cardiac synchronous component. Accordingly, to obtain respiratory information from the thoracic impedance, a process for extracting the component (respiratory component) related to respiratory information in the thoracic impedance is necessary. Since the cardiac synchronous component included in the thoracic impedance data is shorter in cycle than the respiratory rate and easy to be detected, the cardiac synchronous component is extracted first, and the respiratory component is calculated by subtracting the cardiac synchronous component from the thoracic impedance. A change in respiratory status can be detected from a change in such calculated respiratory component of the thoracic impedance.

Figure 7:
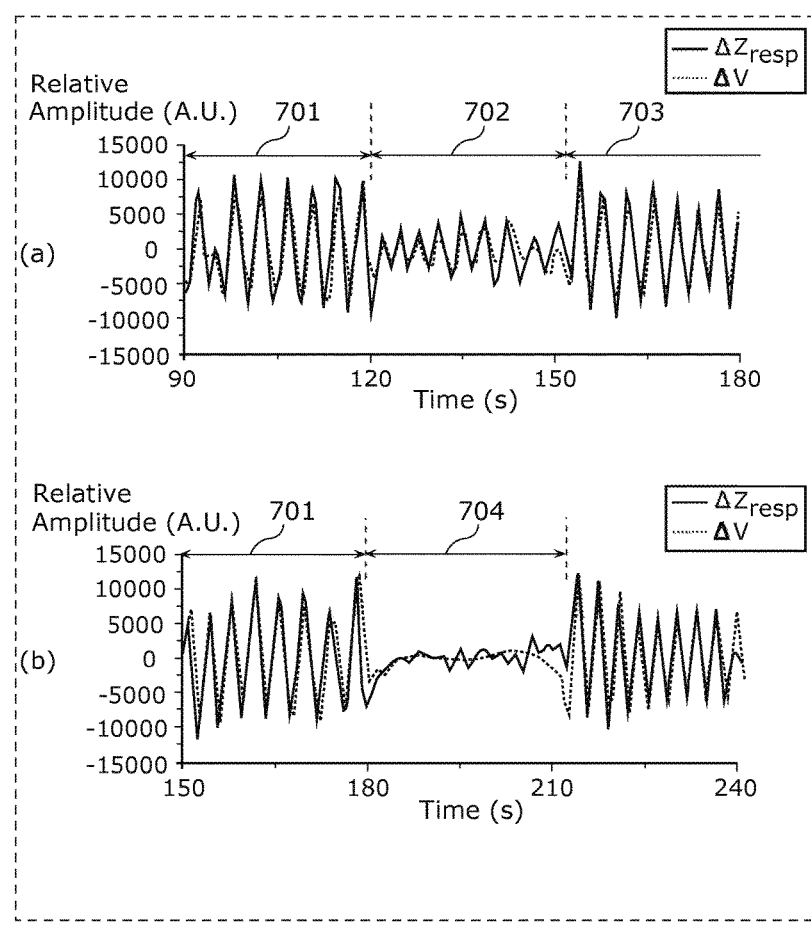
FIG. 7 is an explanatory diagram of a change in impedance when the respiratory status changes.

FIG. 7 is an explanatory diagram of a change in impedance when the respiratory status changes. In FIG. 7, the horizontal axis represents the time, and the vertical axis represents the amount of change in impedance, (a) in FIG. 7 shows an example in the case where a normal respiratory status 701, a slow respiratory status 702, and a normal respiratory status 703 occur in this order. As shown in the drawing, the amplitude of the impedance is lower in the slow respiratory status. (b) in FIG. 7 shows an example in the case where a normal respiratory status and an obstructive apnea status 704 occur in this order. As shown in the drawing, the amplitude of the impedance is lost in the obstructive apnea status 704. Thus, the impedance change reflects not only the respiratory rate but also the expiratory volume.

(Overall Process)

Figure 8:
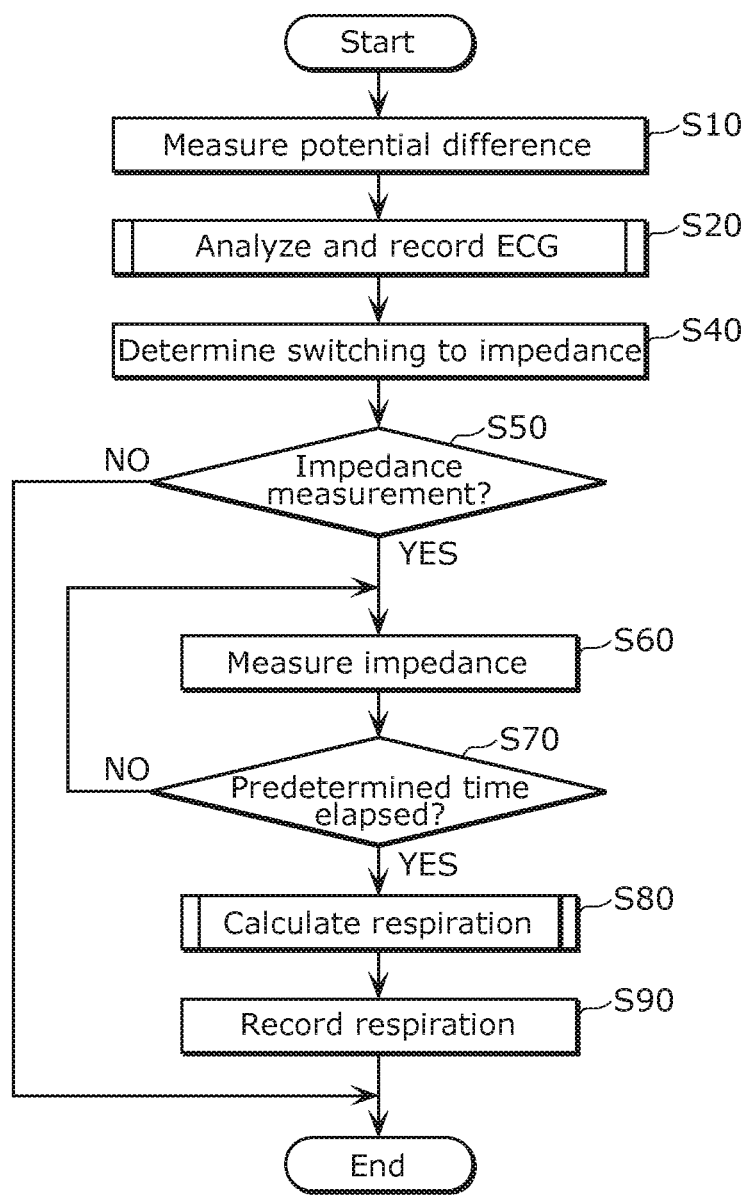
FIG. 8 is a flowchart showing an operation of a biosignal measurement apparatus according to Embodiment 1.

FIG. 8 is a flowchart showing an operation of the biosignal measurement apparatus 110 according to this embodiment. Part of the steps in the flowchart shown in FIG. 8 will be described in detail later.

(Step S10)

The potential difference measurement unit 3 measures the potential difference between the electrodes 2A and 2B attached to the chest of the user 1, as the cardiac potential.

For example, the cardiac potential is recorded as a potential change of about 1 mV at the maximum. The potential difference measurement unit 3 may include the bioamplifier 211 which is a biosignal amplification circuit.

The potential difference is sampled at, for example, 1024 Hz or 512 Hz. Data at each sampling point is submitted to the next step.

(Step S20)

The ECG analysis unit 5 analyzes the potential difference measured by the potential difference measurement unit 3, to obtain the ECG. The ECG analysis unit 5 may record the obtained ECG in the ECG recording unit 6. The process of recording the obtained ECG in the ECG recording unit 6 may be omitted.

For example, the ECG analysis includes calculating the heart rate. The heart rate is calculated from an RR interval which is a time interval between two adjacent R waves in the ECG.

Figure 9:
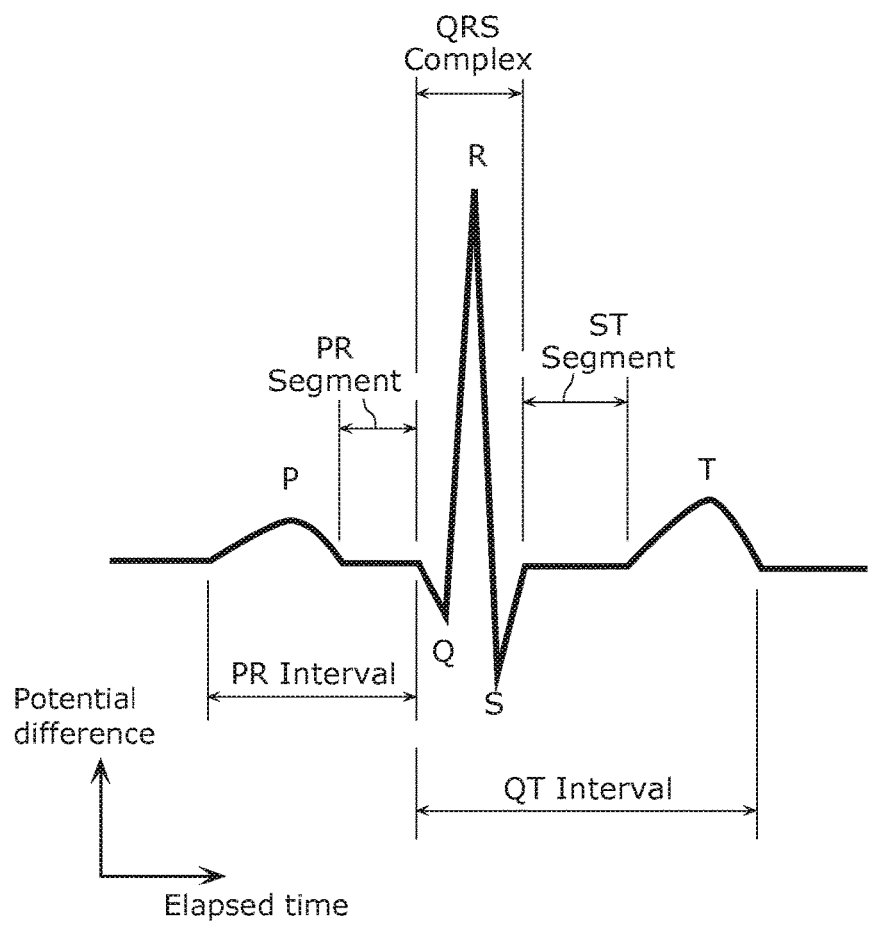
FIG. 9 is a schematic diagram of an ECG waveform.

FIG. 9 is a schematic diagram of an ECG waveform.

A change in ECG waveform for one beat is shown in FIG. 9. The ECG includes ECG waveforms of a plurality of beats. That is, the ECG represents potential changes where the ECG waveform shown in FIG. 9 is repeated. A point at which the amplitude is highest in the waveform is called "R wave". The heart rate is calculated from the time interval (RR interval) between this R wave and its adjacent R wave. Detailed flow of heart rate calculation will be described later.

(Step S40)

The impedance measurement switching unit 7 determines whether or not to switch the measurement to impedance measurement.

In detail, the impedance measurement switching unit 7 determines whether or not to switch the measurement to impedance measurement, based on whether or not the peak of the R wave necessary for heart rate calculation is included in the most recent data measured in Step S10. The impedance measurement switching unit 7 determines to switch the measurement to impedance measurement, immediately after the peak of the R wave is detected.

(Step S50)

The process branches depending on whether or not the impedance measurement switching unit 7 determines to perform impedance measurement. In the case where the impedance measurement switching unit 7 determines to perform impedance measurement (YES), the process proceeds to Step S60. In the case where the impedance measurement switching unit 7 determines not to perform impedance measurement (NO), the process ends.

(Step S60)

The impedance measurement unit 4 performs impedance measurement. In the impedance measurement, the impedance is measured from the voltage value between the electrodes 2A and 2B while applying an extremely weak current between the electrodes 2A and 2B from the current application unit 8.

(Step S70)

The impedance measurement switching unit 7 determines whether or not a predetermined time has elapsed. As an example, a determination condition is defined so that the measurement is switched from impedance measurement back to potential difference measurement when the predetermined time has elapsed. For instance, the predetermined time may be set arbitrarily in a time range from 200 ms to 350 ms, or set to 300 ms.

(Step S80)

The respiratory calculation unit 9 calculates the respiratory rate. The respiratory variation is obtained from the most recent impedance variation data, and converted to the number of breaths per minute. This process will be described in detail later.

(Step S90)

The respiratory calculation unit 9 records respiratory data in the respiratory recording unit 10. For example, the respiratory data includes at least one of the impedance variation and the respiratory rate. The process in this step may be omitted.

By the process described above, ECG information and impedance information are collected from the electrode unit 2 and recorded, Repeatedly performing this process achieves continuous recording of ECG information and impedance information.

(Individual Processes)

The following describes the processes of the ECG analysis unit 5, the impedance measurement switching unit 7, and the respiratory calculation unit 9 in detail, using flowcharts and diagrams.

(Process of the ECG Analysis Unit 5)

Figure 10:
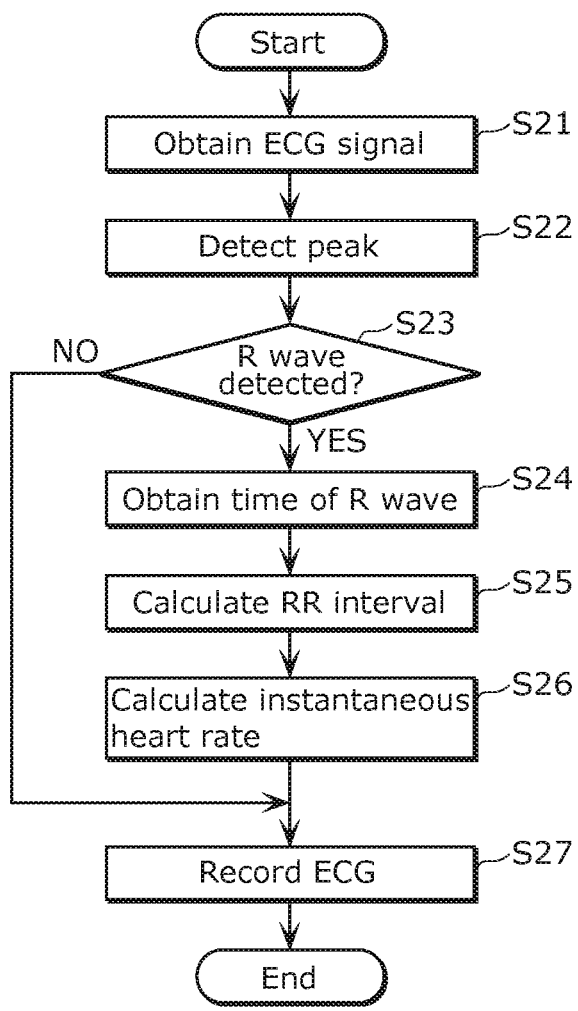
FIG. 10 is a flowchart showing an operation of an ECG analysis unit.

FIG. 10 is a flowchart showing an operation of the ECG analysis unit 5.

(Step S21)

The ECG analysis unit 5 obtains the ECG signal from the potential difference measurement unit 3. The potential difference measurement unit 3 samples the potential difference at a predetermined frequency such as 1024 Hz, and the ECG analysis unit 5 receives the data. Here, the ECG analysis unit 5 need not necessarily obtain data of each sampling point, and may obtain data at appropriate intervals, e.g. data sampled during 100 ms at intervals of 100 ms. The ECG signal desirably includes a plurality of R waves.

(Step S22)

The ECG analysis unit 5 detects a peak. The ECG analysis unit 5 performs peak detection in the ECG, based on previously obtained ECG data and newly obtained ECG data. A peak that is observed most clearly is an R wave, and the ECG analysis unit 5 determines whether or not the R wave is included in the current waveform. Since the feature of the R wave is that the amplitude sharply increases and then sharply decreases soon afterward, the determination can be made based on criteria such as the amplitude and the rate of change of the ECG.

(Step S23)

The ECG analysis unit 5 determines whether or not the R wave is detected. For example, the ECG analysis unit 5 determines that the R wave is detected in the case where the potential of the detected peak is greater than or equal to a predetermined threshold, and determines that the R wave is not detected in the case where the potential of the detected peak is less than the predetermined threshold.

In the case where the ECG analysis unit 5 determines that the R wave is detected, the process proceeds to Step S24. In the case where the ECG analysis unit 5 determines that the R wave is not detected, the process proceeds to Step S27.

(Step S24)

The ECG analysis unit 5 obtains the time of appearance of the R wave. Since the sampled ECG data is associated with time, the ECG analysis unit 5 obtains the time of the peak of the R wave.

(Step S25)

The ECG analysis unit 5 calculates an RR interval, from the difference between the time at which the immediately previous R wave is obtained and the time at which the current R wave is obtained.

(Step S26)

The ECG analysis unit 5 calculates an instantaneous heart rate. The instantaneous heart rate is a heart rate per minute if the RR interval calculated in Step S25 is maintained, and is calculated as "(60 (seconds))/(RR interval (seconds))". For example, the instantaneous heart rate is 60 when the RR interval is 1 second, and 120 when the RR interval is 0.5 second.

(Step S27)

The ECG analysis unit 5 sends the measurement data to the ECG recording unit 6. The data sent here is at least one of the data of the newly obtained ECG signal and the data of the instantaneous heart rate.

Though the R wave is detected using the peak potential in Steps S22 and S23, a known R wave detection method may be used. For example, a waveform part included in the obtained ECG may be compared with an R-wave waveform template held beforehand, to determine their similarity. A waveform in the ECG having at least predetermined similarity may be detected as the R wave.

Repeatedly performing such a process achieves continuous measurement of ECG information. This is described in more detail below, with reference to FIG. 11.

Figure 11:
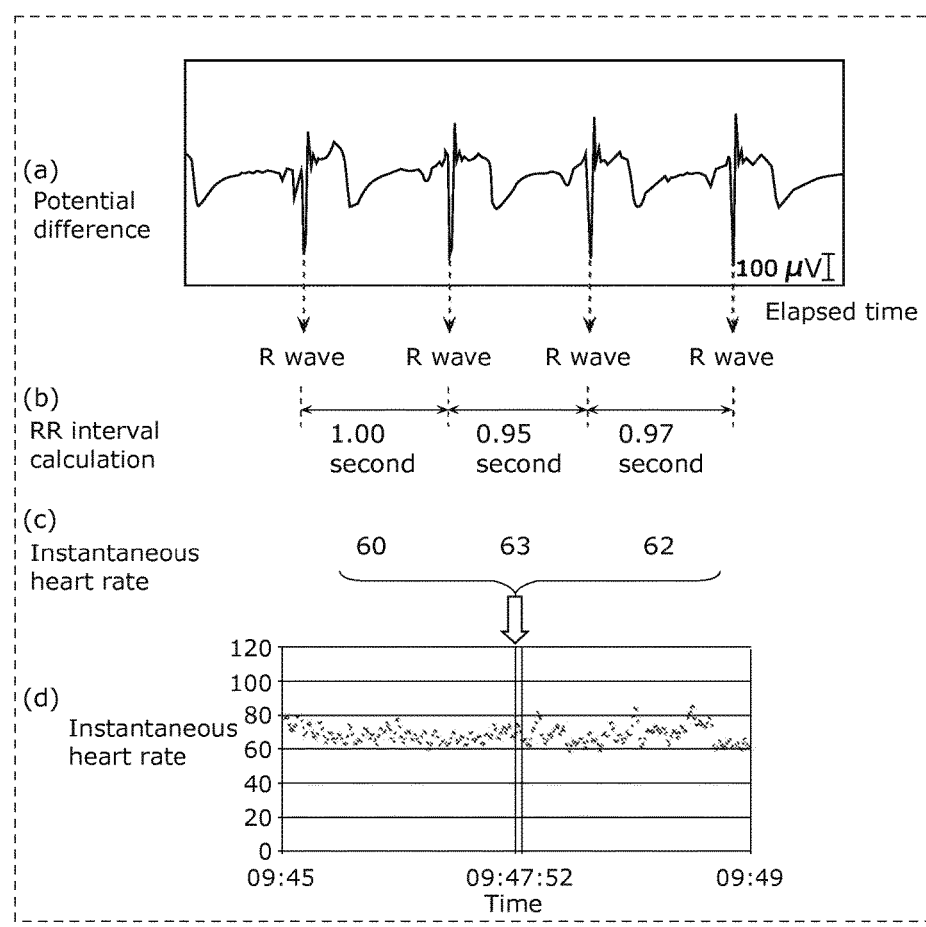
FIG. 11 is an explanatory diagram of calculation of a heart rate from an ECG.

FIG. 11 is an explanatory diagram of calculation of the heart rate from the ECG.

(a) in FIG. 11 shows an example of the measured ECG. The ECG waveform is recorded in various shapes depending on the electrode position. The R wave is detected based on the changing waveform of the ECG. The R wave is a point at which the amplitude changes especially sharply in a short time in the ECG, and is detectable based on a combination of an amplitude change greater than or equal to a predetermined threshold and an amplitude change in a short time. The position of each R wave is shown in (a) in FIG. 11.

(b) in FIG. 11 shows the RR interval calculation method. For example, three RR intervals can be defined with regard to four R waves. The intervals can be calculated at, for instance, 1.00 second, 0.95 second, and 0.97 second.

(c) in FIG. 11 shows the instantaneous heart rate calculation method. The instantaneous heart rate is a heart rate per minute if the most recent RR interval is repeated for 1 minute, and can be calculated as "(60 (seconds))/(RR interval (seconds))". In the above-mentioned example of the RR intervals, the instantaneous heart rates are calculated at 60, 63, and 62.

(d) in FIG. 11 shows the time change of the instantaneous heart rate. Since the instantaneous heart rate can be plotted each time the R wave is detected, as many points as heartbeats are plotted.

(Process of the Impedance Measurement Switching Unit 7)

Figure 12:
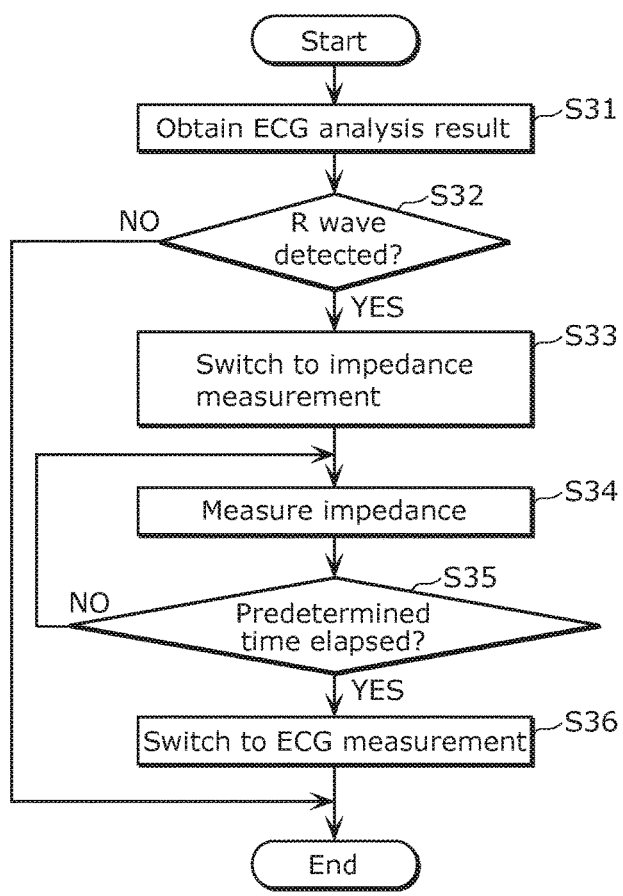
FIG. 12 is a flowchart showing an operation of an impedance measurement switching unit.

The process of the impedance measurement switching unit 7 is described in detail below. FIG. 12 is a flowchart showing an operation of the impedance measurement switching unit 7. The flowchart shown in FIG. 12 focuses on the operation of the impedance measurement switching unit 7 in Steps S40 to S70 in the flowchart shown in FIG. 8.

(Step S31)

The impedance measurement switching unit 7 obtains the ECG analysis result from the ECG analysis unit 5. The ECG analysis result indicates whether or not the R wave is detected by the time of this process. For example, the ECG analysis result includes time information of R wave detection closest to the current time.

(Step S32)

The impedance measurement switching unit 7 determines whether or not the R wave is detected by the ECG analysis unit 5. For instance, the impedance measurement switching unit 7 determines whether or not the R wave is included in a predetermined time period. An example of the predetermined time period is predetermined time before the current time. The impedance measurement switching unit 7 may record the predetermined time period related to R wave detection beforehand, or receive the predetermined time period from an external recording unit.

In the case where the R wave is detected, the process proceeds to Step S33. In the case where the R wave is not detected, the process ends.

Here, a predetermined time period that includes the time at which the R wave is detected is referred to as "period including the R wave". On the other hand, a time period that is included in the duration from the time at which the R wave is detected to the time at which the next R wave is expected to be detected and that is other than the period including the R wave is referred to as "period not including the R wave". The period not including the R wave is also referred to as "first period", and the period including the R wave is also referred to as "second period". Typically, the first period and the second period alternate in the ECG waveform.

For example, the impedance measurement switching unit 7 receives the time at which the R wave is detected and the duration of the RR interval from the ECG analysis unit 5, and determines the period including the R wave and the period not including the R wave. The impedance measurement switching unit 7 may determine whether or not the R wave is detected, based on whether or not the second period is included in the predetermined time period before the current time.

(Step S33)

In the case where the R wave is detected, the impedance measurement switching unit 7 performs a process for switching the measurement to impedance measurement.

The biosignal measurement apparatus 110 has a function of measuring both the potential difference and the impedance between the electrodes 2A and 2B, and is switched from potential difference measurement to impedance measurement by the process in this step.

(Step S34)

The impedance measurement switching unit 7 controls the impedance measurement unit 4 to measure the impedance. For impedance measurement, an extremely weak current is passed through the human body. The impedance is measured while applying an extremely weak current between the electrodes 2A and 2B. The extremely weak current may be applied from the current application unit 8.

(Step S35)

The impedance measurement switching unit 7 calculates an elapsed time from when the impedance measurement unit 4 starts impedance measurement, and determines whether or not a predetermined time has elapsed. The impedance measurement switching unit 7 may record the predetermined time related to the impedance measurement time beforehand, or receive the predetermined time from an external recording unit.

If only the impedance is measured for a long time, the next R wave cannot be detected. Hence, the measurement needs to be switched back to ECG measurement in the case where the predetermined time has elapsed from the impedance measurement start. Given that a normal human heart rate ranges approximately from 60 to 200, the next R wave is expected to be detected 0.3 second to 1 second after the detection of the current R wave. The predetermined elapsed time for impedance measurement can therefore be set to 0.3 second or more. The time until the next R wave is detected varies depending on the heart rate. In view of this, the time is corrected according to age, whether or not the user is exercising, or the like, with it being possible to build a system capable of impedance measurement while detecting each R wave.

In the case where there is a need to monitor heart disease, the switching interval may be shortened because the cardiac potential needs to be measured more accurately.

(Step S36)

When the predetermined time has elapsed from the impedance measurement start, the impedance measurement switching unit 7 switches the measurement to ECG measurement for detecting the next R wave.

Repeatedly performing such a process achieves measurement of both the impedance and the cardiac potential while switching between impedance measurement and cardiac potential measurement. It is thus possible to detect the timing of the R wave in the ECG and also measure respiratory information.

Figure 13:
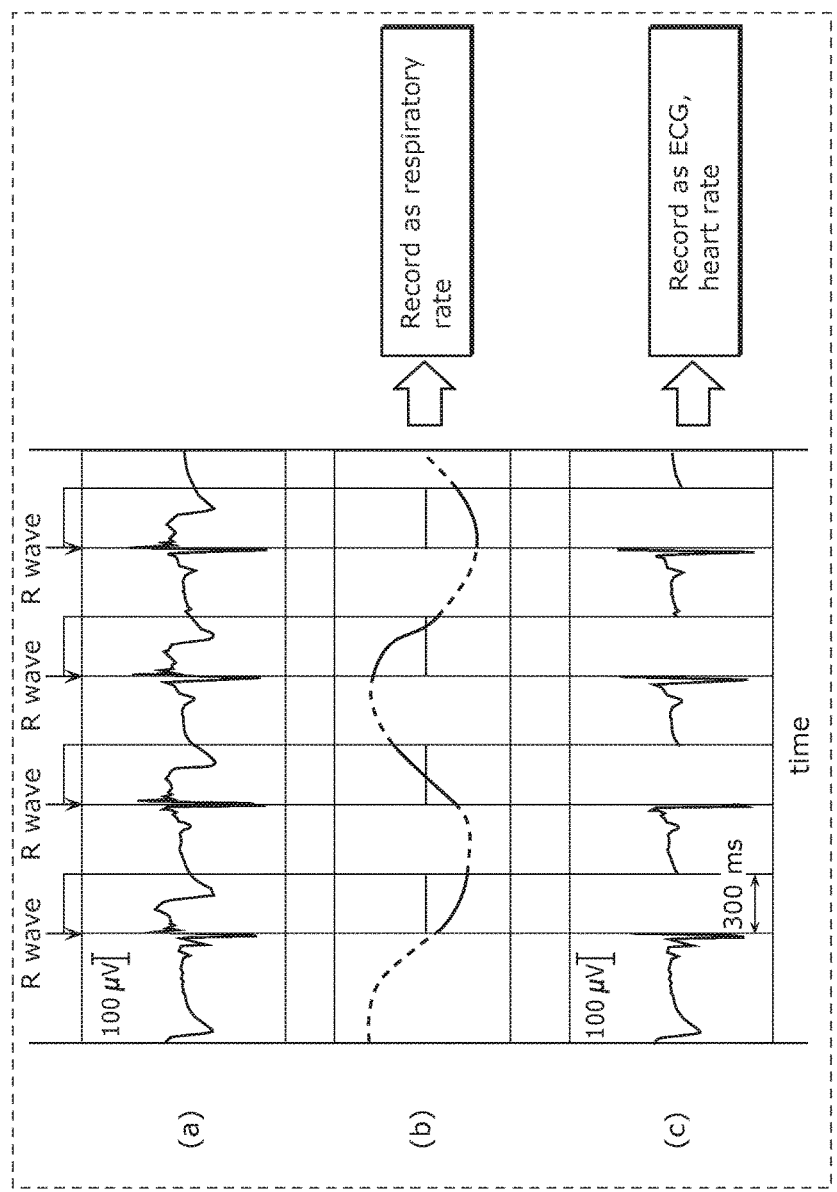
FIG. 13 is an explanatory diagram of data obtained by the biosignal measurement apparatus according to Embodiment 1.

FIG. 13 is an explanatory diagram of data obtained by the biosignal measurement apparatus according to Embodiment 1. (a) in FIG. 13 shows an example of data in the case of measuring only the ECG. Typically, data as shown in (a) in FIG. 13 is obtained in the case of measuring only the ECG. The waveform may take various shapes depending on the electrode position. The R wave is a point at which the amplitude changes sharply. In (a) in FIG. 13, the measurement is switched to impedance measurement at the timing of the R wave. (b) in FIG. 13 shows impedance measurement data measured at the timing controlled by the impedance measurement switching unit 7. The solid line represents the measurement data. The dotted line represents data in a period in which measurement is not actually performed, i.e. data obtained by temporally interpolating (hereafter simply referred to as "interpolating") the data represented by the solid line. (c) in FIG. 13 shows a record of ECG measured at the timing controlled by the impedance measurement switching unit 7. As shown in the drawing, the ECG is recorded only when the impedance is not measured. This embodiment has a feature that the accurate RR interval can be calculated based on such an ECG in the same way as calculating the RR interval based on the complete ECG shown in (a) in FIG. 13.

(Process of the Respiratory Calculation Unit 9)

Figure 14:
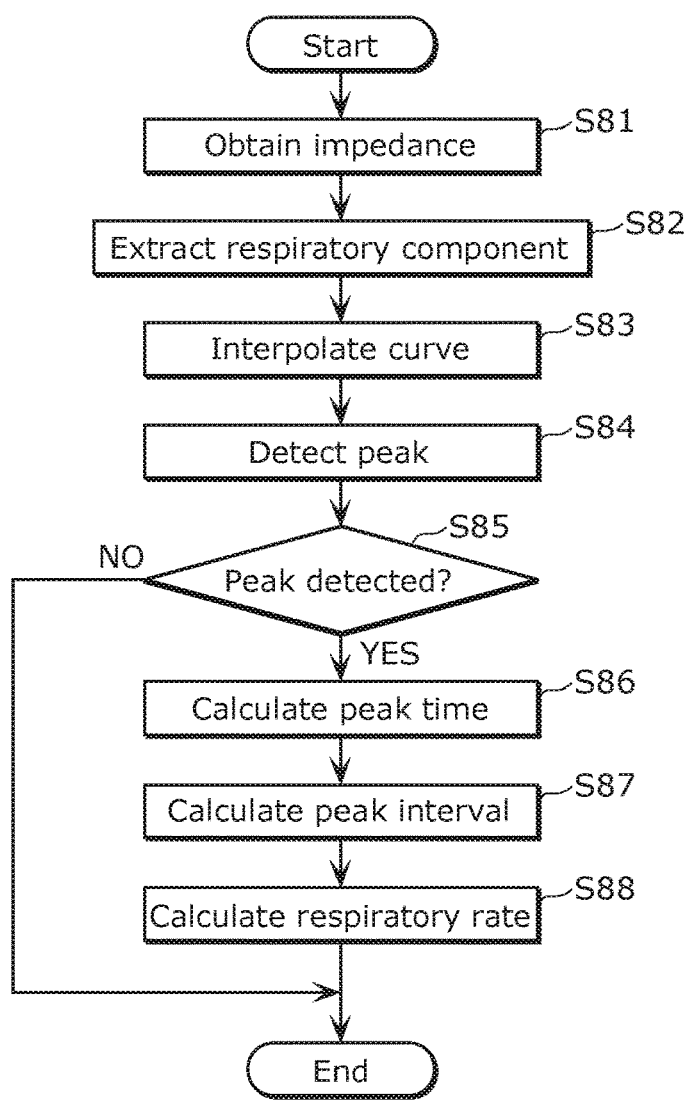
FIG. 14 is a flowchart showing an operation of a respiratory calculation unit.

FIG. 14 is a flowchart showing an operation of the respiratory calculation unit 9. The process of the respiratory calculation unit 9 is described in detail below, with reference to FIG. 14.

(Step S81)

The respiratory calculation unit 9 obtains the impedance value from the impedance measurement unit 4. The obtained impedance value covers a time section from the previous obtainment to the current time. Here, intermittently measured data is obtained because the impedance is not constantly measured as shown in (b) in FIG. 13.

(Step S82)

The respiratory calculation unit 9 extracts the respiratory component from the impedance information obtained in Step S81. The impedance information obtained in Step S81 includes ECG-related information derived from the motion of the heart, body movement information, respiratory information, and the like. It is therefore necessary to filter only the respiration-derived component. Here, the component obtained by removing the ECG-related component from the source signal of the measured impedance value by an adaptive filter may be used as described in NPL 1. The component corresponding to respiration can be extracted as a result of the process in NPL 1.

Figure 15:
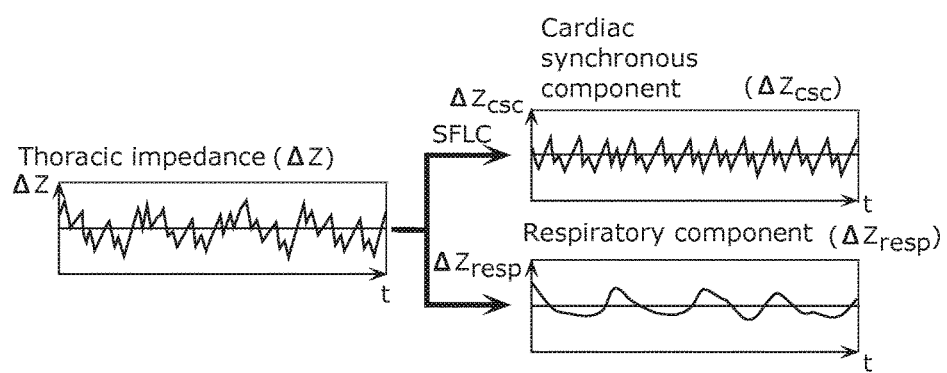
FIG. 15 is an explanatory diagram of a method of conversion from an impedance to a respiratory rate.

The respiratory component extraction method is described in more detail below, with reference to FIG. 15. FIG. 15 is an explanatory diagram of a method of conversion from the impedance to the respiratory rate. As shown in the drawing, the respiratory component can be calculated by extracting the cardiac synchronous component from the thoracic impedance by an adaptive filter (SFLC: Scaled Fourier Linear Combiner) and finding the difference between the thoracic impedance component and the cardiac synchronous component.

(Step S83)

The respiratory calculation unit 9 performs an interpolation process on the impedance signal including the respiratory component obtained in Step S82. Performing a curve interpolation process on the intermittently obtained impedance signal enables obtainment of a continuous respiration-related waveform. An example of the curve as a result of the interpolation process is a waveform connecting the dotted line and the solid line in (b) in FIG. 13. The timing of switching between expiration and inspiration is detectable by this process.

(Step S84)

The respiratory calculation unit 9 detects a peak in the continuous respiration-related waveform obtained in Step S83. It is known that the respiration-related impedance changes synchronously with respiration. Accordingly, a point of change from an expiratory state to an inspiratory state or from an inspiratory state to an expiratory state can be detected as a result of peak detection.

(Step S85)

The respiratory calculation unit 9 determines the result of peak detection. In the case where the peak is not detected, the process of the respiratory calculation unit 9 ends on the ground that information related to respiratory rate detection is not obtained in the current impedance obtainment process section. In the case where the peak is detected, the process proceeds to Step S86.

(Step S86)

The respiratory calculation unit 9 converts a sampling time at peak detection, to a measurement time.

(Step S87)

The respiratory calculation unit 9 calculates a peak interval. The respiratory calculation unit 9 stores a measurement time at the previous peak detection, and calculates a time required for one breath from the difference between the previous peak detection time and the current peak detection time.

(Step S88)

The respiratory calculation unit 9 calculates the respiratory rate. Through the use of the time required for one breath, the respiratory rate in the case of assuming that this breath is repeated for 1 minute is calculated as "(60 (seconds))/(required breath time (seconds))".

By the process described above, the respiratory calculation unit 9 calculates the respiratory rate from the impedance information measured by the impedance measurement unit 4, and records the respiratory rate in the respiratory recording unit 10. Thus, both heart rate information and respiratory rate information can be continuously measured by measuring both the potential difference and the impedance using the same electrodes while switching the measurement at appropriate timings.

Here, a preliminary measurement period (e.g. 1 minute or 2 minutes) which is a period for measuring only the ECG may be provided at an initial stage of measurement or a predetermined stage during measurement. The subsequent timing of switching to the impedance measurement period may then be adjusted based on the result of analyzing the ECG in the preliminary measurement period. A method of controlling the switching timing based on the ECG analysis result is described in detail below.

When premature atrial contraction is observed from the ECG analysis result, a heart rate about twice a normally expected heart rate is set. Premature atrial contraction is detected as a phenomenon that a fast heartbeat suddenly appears in substantially regular RR intervals. In such a case, if measurement is performed based on the normally expected heart rate, there is a possibility that an R wave due to premature atrial contraction cannot be measured. Therefore, the heart rate about twice the normally expected heart rate is set to enable measurement of an R wave due to premature atrial contraction.

When an abnormality is observed in a P wave in the ECG analysis result, the timing of switching to the impedance measurement period is set so that the P wave immediately preceding the R wave is also included in the ECG measurement range. Moreover, the measurement is switched to impedance measurement immediately after the R wave so that the ECG measurement period does not overlap with the impedance measurement period. Specific examples of the P wave abnormality include a situation where the waveform of the P wave is lost and the P wave is unrecognizable in the ECG, and a situation where a waveform different from the typical waveform of the P wave is measured. In such a case, an ST wave may be excluded from impedance measurement, Particularly in the case where the waveform of the P wave is lost, the R wave appears suddenly, and so it is effective to reduce the impedance measurement time.

When an abnormality is observed in an ST wave in the ECG analysis result, the timing of switching to the impedance measurement period is set so that the ST wave is also included in the ECG measurement range. Moreover, the ECG measurement period is kept from overlapping with the impedance measurement period. The measurement may be switched to impedance measurement not immediately after the R wave but after the measurement of the ST wave ends. Specific examples of the ST wave abnormality include a situation where the amplitude of the ST wave increases or decreases more than normal. In such a case, a P wave may be excluded from impedance measurement. It is particularly effective to measure the impedance during a period other than when the P wave and the ST wave appear.

Note that an atrial abnormality is suspected in the case where the P wave is abnormal, and myocardial ischemic is suspected in the case where the ST wave is abnormal.

Advantageous Effects

By alternately performing potential measurement and impedance measurement in a time division manner using the same electrode set according to the structures and processes described above, it is possible to easily measure heart rate information and respiratory rate information without attaching a sensor to the user in addition to the electrodes used when measuring only the potential.

Though the impedance measurement duration is set as a predetermined time of 0.3 second from R wave detection in the impedance measurement switching unit 7, other switching methods may be used. Since diagnostic information is also obtained from waveforms other than the R wave in the ECG, the impedance measurement time may be set to a short time such as several tens of milliseconds to 100 milliseconds in the case of collecting data with emphasis on the ECG. This can vary depending on the time required for switching. Typically, the heart rate is higher than the respiratory rate. Accordingly, the respiratory rate can be estimated to a certain extent so long as impedance data of a relatively short time is available for each heartbeat's R wave.

In respiratory measurement by the impedance method, information related to the expiratory volume is obtained, too. Therefore, in the case of maximizing the impedance change section, the impedance measurement time sufficiently long to detect the next R wave may be set by estimating the timing of the next R wave based on the current RR interval, instead of setting the impedance measurement duration to the predetermined time. This is possible because the RR interval does not suddenly change significantly and so an interval similar to the current RR interval is expected.

In the structure of wirelessly transmitting the measurement data using the transmission unit 240 as shown in FIG. 5, the above-mentioned signal processing for ECG analysis, impedance switching, respiratory calculation, and the like may be performed in the biosignal measurement system 100w, or a reception apparatus to which the measurement data is wirelessly transmitted. That is, instead of performing the above-mentioned signal processing in the biosignal measurement system 100, the data may be first transmitted from the transmission unit 240 to a PC or the like on the data reception side so that the signal processing is performed in the receiving PC. Executing complex signal processing in the signal processing unit 220 in the biosignal measurement system 100 increases the power consumption of the CPU and the like. Since the data transmission amount and the power consumption are proportional in the transmission unit 240, which of the PC and the biosignal measurement system 100w performs the signal processing and how much data is transmitted in order to carry out long-time monitoring may be set suitably according to application.

As described above, the biosignal measurement apparatus can successively obtain heartbeat information by ECG measurement and respiratory information by impedance measurement in a time division manner using the same electrodes. Here, respiration is measured in the period not including the R wave which is a characteristic waveform in the ECG. Thus, measurement data for the period that includes information necessary for obtainment of heartbeat information is obtained in the ECG measurement period, and measurement data other than the above-mentioned measurement data is obtained in the impedance measurement period. Respiratory information and heartbeat information can be simultaneously obtained in this way.

Moreover, the R wave which is a characteristic waveform in the ECG can be included in the ECG measurement result. By detecting the R wave in the ECG measurement result, it is possible to obtain heartbeat-related information such as a heart rate and a heartbeat depth. This enables more accurate heart rate measurement.

Moreover, the heart rate can be calculated based on the time interval between the R waves included in the ECG measurement result. This enables more accurate heart rate measurement.

Moreover, the start timing of the period for respiratory measurement can be determined based on the R wave included in the ECG measurement result. The determination of the start timing of the period for respiratory measurement also corresponds to estimating the start timing of the next period for respiratory measurement using the already measured ECG. Since the heartbeat cycle changes from moment to moment, it is impossible to set the period for respiratory measurement in a predetermined constant cycle. Accordingly, the start timing of the period for respiratory measurement is set based on the time of the R wave in a period of one heartbeat. Thus, the period for respiratory measurement can be set in the period not including the R wave, in each heartbeat period.

Moreover, a continuous impedance measurement result can be obtained by temporally interpolating impedance measurement results in a plurality of separate periods. Information related to respiration can then be obtained from the impedance measurement result.

Moreover, the length of the period for respiratory measurement can be determined based on the time interval between the R waves included in the ECG measurement result. Since the heartbeat cycle changes from moment to moment, it is impossible to set the period for respiratory measurement in a predetermined constant cycle. Accordingly, the length of the period for respiratory measurement is set based on the time of the R wave in a period of one heartbeat. Thus, the period for respiratory measurement can be set in the period not including the R wave, in each heartbeat period.

Moreover, the electrodes used for measuring the potential difference can also be used for measuring the impedance. Impedance measurement can be performed with no need to use new electrodes in addition to the electrodes used when performing ECG measurement. Respiratory information and heartbeat information can be simultaneously obtained in this way.

Moreover, in the case where an abnormality or the like is detected based on the ECG continuously measured in the preliminary period, the start timing and the length of the period for respiratory measurement can be adjusted so that the abnormality is not included in the period for respiratory measurement, i.e. the abnormality is included in the ECG.

Moreover, in the case where an abnormality is detected in the P wave or the ST wave in the ECG continuously measured in the preliminary period, the start timing and the length of the period for respiratory measurement can be adjusted so that the P wave or the ST wave having the abnormality is not included in the period for respiratory measurement, i.e. the P wave or the ST wave is included in the ECG together with the R wave.

Embodiment 2

This embodiment describes another example of the respiratory rate estimation method of the respiratory calculation unit 9.

The first period and the second period alternate in the ECG, as mentioned earlier. Accordingly, in the case where the impedance is measured in the first period, the impedance measurement result is obtained intermittently. The respiratory waveform needs to be estimated in order to estimate the respiratory component from the impedance measurement result. However, if the time section of the obtained impedance measurement data is not sufficiently long, the respiratory waveform may not be accurately estimated. This is because the respiratory cycle can be several seconds to several tens of seconds per breath in deep respiration and can be one second or less per breath in respiration after exercise.

For instance, the human heart rate varies in a range of about 40 to 200 beats per minute, i.e. varies in a range of about fivefold. Besides, a heart rate of 40 to 180 is required to be measured as an example.

On the other hand, the respiratory rate varies in a range of about 5 or 6 to 100 breaths per minute, i.e. varies in a range of tenfold or more. Thus, the range of variation of the respiratory rate is greater than the range of variation of the heart rate. This makes the estimation of the respiratory rate difficult.

Figure 16:
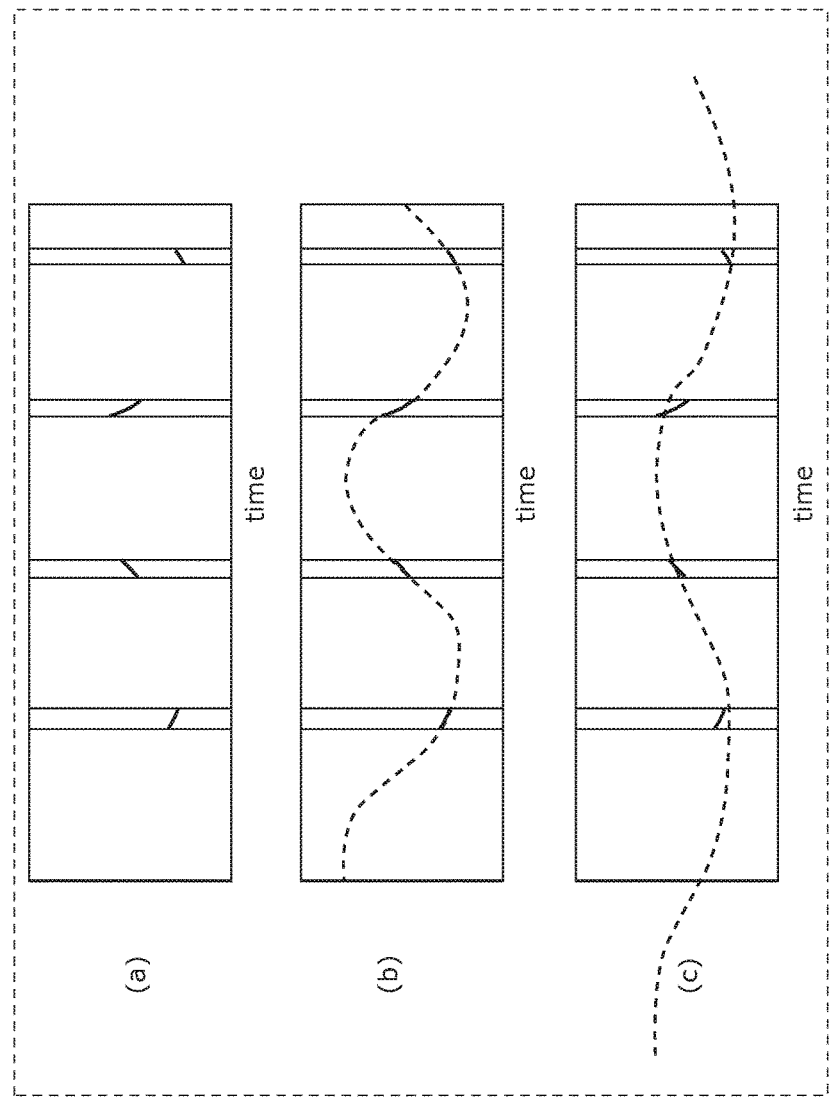
FIG. 16 is a diagram showing an example of respiratory rate estimation.

FIG. 16 is a diagram showing an example of respiratory rate estimation. (a) in FIG. 16 shows a measured impedance signal. In the case of putting emphasis on the ECG and obtaining data for performing ECG measurement for a relatively long time, the time section in which the impedance signal is obtained tends to be short as in (a) in FIG. 16. (b) in FIG. 16 shows an example of an estimation curve of the measured impedance. The curve designated by the dotted line is the estimation curve in the case of respiration in the same cycle as in (b) in FIG. 13. (c) in FIG. 16 is another example of the estimation curve of the measured impedance. In the case where the time of the impedance signal is short, the estimation curve as shown in (c) in FIG. 16 is possible, too. The respiratory information obtained from (c) in FIG. 16 indicates slower and shallower respiration than that from (b) in FIG. 16. Thus, there is a situation where a plurality of estimation curve candidates exist and it is difficult to uniquely determine the estimation curve.

This embodiment describes an example of a method for more accurately estimating the respiratory waveform. While the result obtained by the ECG analysis unit 5 is used only for impedance measurement switching in Embodiment 1, Embodiment 2 differs from Embodiment 1 in that the information obtained by the ECG analysis unit 5 is also used in the respiratory calculation unit 9.

Figure 17:
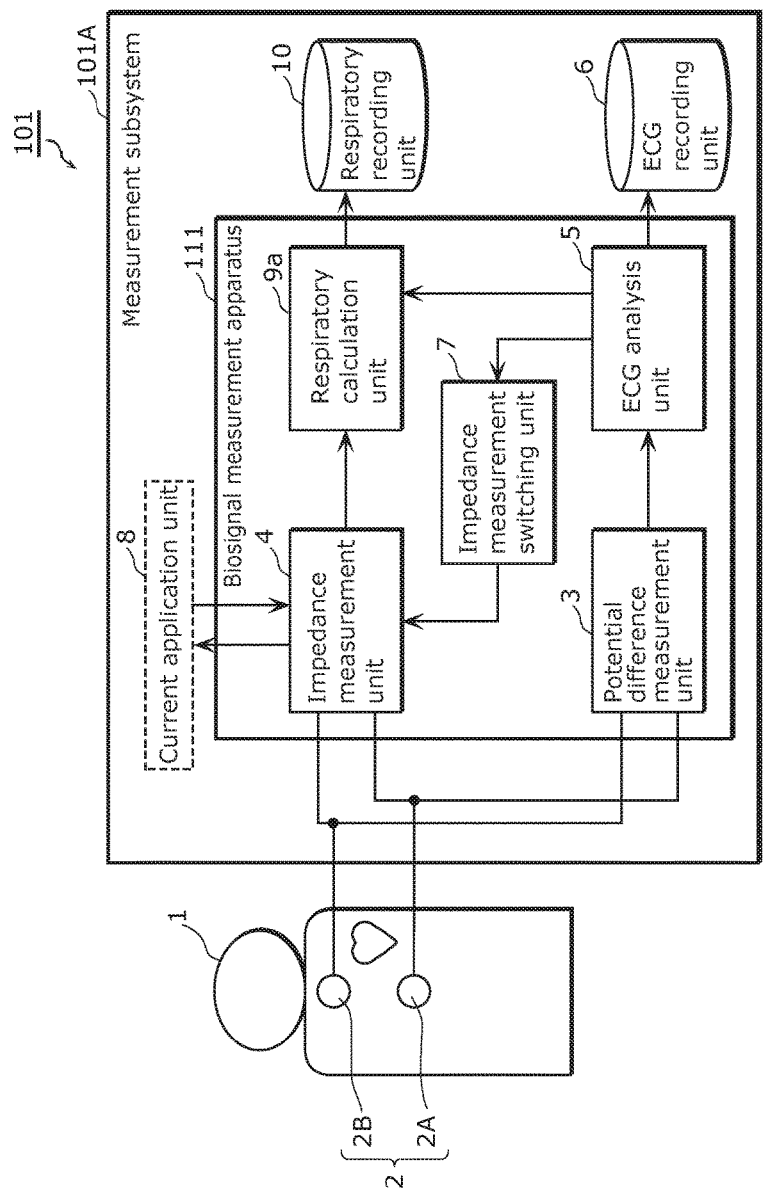
FIG. 17 is a diagram showing an example of a functional structure of a biosignal measurement system according to Embodiment 2.

FIG. 17 is a diagram showing an example of a functional structure of a biosignal measurement system 101 according to this embodiment. The difference from Embodiment 1 lies in that a respiratory calculation unit 9a is included instead of the respiratory calculation unit 9. A calculation method used in the respiratory calculation unit 9a is different from that in the respiratory calculation unit 9. The following mainly describes the process of the respiratory calculation unit 9a.

Figure 18:
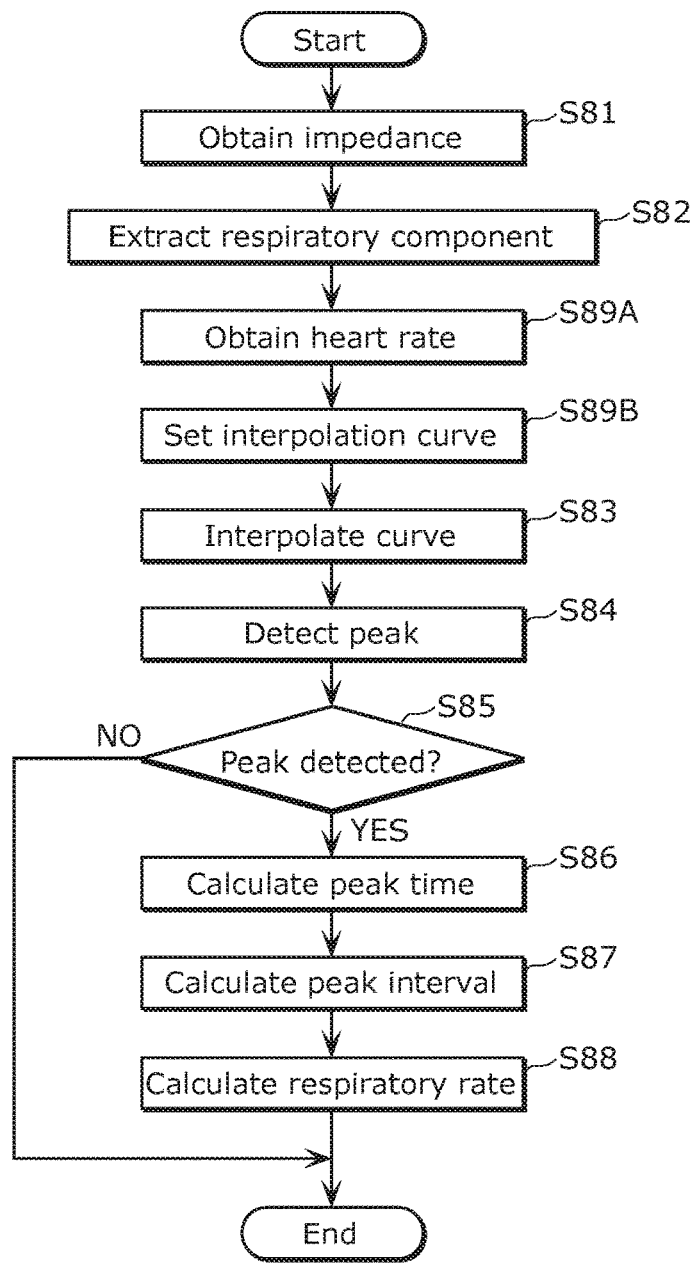
FIG. 18 is a flowchart showing an operation of a respiratory calculation unit.

FIG. 18 is a flowchart of the respiratory calculation unit 9a in the biosignal measurement system 101 according to this embodiment. Though the flow is basically the same as that in FIG. 14, Steps S89A and S89B are added between Steps S82 and S83. Steps S89A and S89B and Step S83 which corresponds to the curve interpolation method are described below.

(Step S89A)

The respiratory calculation unit 9a obtains the current heart rate information from the ECG analysis unit 5. The heart rate information may be the most recent instantaneous heart rate, the average heart rate for the most recent several seconds or several tens of seconds, or the like. Typically, the heart rate and the respiratory rate are positively correlated to each other.

(Step S89B)

The respiratory calculation unit 9a sets an interpolation curve based on the respiratory rate estimated according to the heart rate information. Basically, the cycle of the interpolation curve is set based on the respiratory rate. A normal resting respiratory rate in adults is 16 to 18. Accordingly, when the user currently has a typical heart rate, for example, the respiratory rate is assumed to be around 17. In such a case, the initial value of the number of cycles of the interpolation curve may be set to 17 which is the typical heart rate. In the case where the heart rate is higher than the typical heart rate to a certain extent such as 30% or more, the respiratory rate is assumed to be higher, too. In this case, the number of cycles of the interpolation curve may be set larger, such as about 30. For example, interpolation fails when a waveform for two cycles is erroneously interpreted as a waveform for one cycle. Such an interpolation failure can, however, be avoided by approximately doubling the number of cycles of the interpolation curve beforehand.

In the structure in FIG. 17, the correspondence relations between heart rates and respiratory rates may be stored as a database, to determine the respiratory rate search range.

In Step S83, the respiratory calculation unit 9a performs an interpolation process on the impedance signal including the respiratory component obtained in Step S82. Performing a curve interpolation process on the intermittently obtained impedance signal enables obtainment of a continuous respiration-related waveform. By setting the cycle of the curve interpolation process beforehand in Step S89B, it is possible to avoid confusion with the second harmonic or the third harmonic.

The method of estimating the respiratory rate of the user and setting the cycle of the interpolation curve so as to be closer to the estimate is described in this embodiment. This method can also be expressed as "setting a plurality of curve interpolation process cycles beforehand and selecting, from a plurality of interpolation curves obtained by a plurality of curve interpolation process methods, an interpolation curve that is estimated to match a phenomenon".

Advantageous Effects

By the process described above, the respiratory rate is estimated according to the heart rate information obtained by ECG analysis, with it being possible to reduce respiratory rate estimation errors and more accurately estimate the respiratory rate which varies widely.

While the resting respiratory rate in adults is 16 to 18, the resting respiratory rate is 20 to 30 in toddlers or preschoolers and 30 to 40 in infants. Hence, the cycle of the interpolation curve as the initial value may be modified according to the user's age.

Since it is known that the amplitude and the amount of ventilation are correlated to each other in the respiratory component of the thoracic impedance, the initial value of the interpolation curve may be modified according to the amount of ventilation. For example, in deep respiration, it is expected that the amount of ventilation is large and respiration is slow. In the case where the amount of ventilation is small, on the other hand, the respiratory rate is likely to be high. The initial value of the interpolation curve may be modified in consideration of this. In more detail, both the heart rate and the amplitude of the impedance may be taken into consideration.

As described above, respiratory information that is assumed to be correct can be selected from the plurality of estimated respiratory rate candidates, through the use of the correlation between the heart rate and the respiratory rate. This enables more accurate respiratory rate measurement.

Moreover, respiratory information that is assumed to be correct can be selected from the plurality of estimated respiratory rate candidates, through the use of the correlation between the heart rate and the respiratory depth. This enables more accurate respiratory rate measurement.

Each of the structural elements in each of the above-described embodiments may be configured in the form of an exclusive hardware product, or may be realized by executing a software program suitable for the structural element. Each of the structural elements may be realized by means of a program executing unit, such as a CPU and a processor, reading and executing the software program recorded on a recording medium such as a hard disk or a semiconductor memory. Here, the software program for realizing the biosignal measurement apparatus and the like according to each of the embodiments is a program described below.

The program causes a computer to execute: measuring a potential difference between a plurality of electrodes placed on a user's chest; obtaining an electrocardiogram (ECG) indicating a temporal variation of a cardiac potential of the user, by analyzing the measured potential difference; determining a start timing of a first period which is a period not including an R wave, in a waveform of the obtained ECG; measuring an impedance between the plurality of electrodes in the first period; and calculating respiratory information related to respiration of the user, based on a temporal variation of the measured impedance.

The herein disclosed subject matter is to be considered descriptive and illustrative only, and the appended Claims are of a scope intended to cover and encompass not only the particular embodiment(s) disclosed, but also equivalent structures, methods, and/or uses.

INDUSTRIAL APPLICABILITY

The biosignal measurement apparatus according to one or more exemplary embodiments disclosed herein enables a simpler structure of a biological information monitoring apparatus. Accordingly, information of both an ECG and a respiratory rate, which are conventionally available only through hospitalization or the like, can be evaluated at home, and evaluated for a long time. In detail, the biosignal measurement apparatus is applicable to fields where both heartbeat and respiration are measured, such as simplified measurement at hospitals, health checkup at home, exercise stress state recognition in sports, and so on.

The invention claimed is:
1. A biosignal measurement apparatus comprising:
a potential difference measurement circuit configured to measure a potential difference between a plurality of electrodes placed on a user's chest;
an impedance measurement circuit configured to measure an impedance between the plurality of electrodes in a first period for respiratory measurement of the user, the first period being a period not including an R wave;
a processor; and
a non-transitory computer-readable recording medium having stored thereon executable instructions, which when executed by the processor, cause the biosignal measurement apparatus to:
obtain a first electrocardiogram (ECG) indicating a temporal variation of a cardiac potential of the user, from the potential difference measured by the potential difference measurement circuit;
set a start timing of the first period using the obtained first ECG, the start timing of the first period being set based on a time of an R wave in a period of one heartbeat of the user, such that the first period is set in the period not including the R wave;
determine a length of the first period, based on a time interval between two adjacent R waves in the obtained first ECG;
receive a first time at which the R wave is detected most recently, and determine the length of the first period to cause the first period to be included between the first time and a time at which the time interval between the two adjacent R waves elapses from the first time;
measure a second ECG indicating a temporal variation of a cardiac potential of the user, from the potential difference measured by the potential difference measurement circuit in a second period which is a period including an R wave and not including the first period;
calculate respiratory information related to the respiration measurement of the user, based on a temporal variation of the impedance measured by the impedance measurement circuit;
calculate a heart rate of the user based on a time interval between two adjacent R waves in the obtained first ECG; and
output the calculated respiratory information, the calculated heart rate, and at least one of the first ECG and the second ECG for the diagnosing of diseases,
wherein the executable instructions, when executed by the processor, further cause the biosignal measurement apparatus to:
determine a start timing and a length of a preliminary measurement period which is a period for continuously measuring the cardiac potential of the user,
obtain the temporal variation of the cardiac potential of the user in the preliminary measurement period, from the potential difference measured by the potential difference measurement circuit in the preliminary measurement period, and
determine the start timing and the length of the first period, based on the temporal variation of the cardiac potential of the user in the preliminary measurement period, and
wherein the executable instructions, when executed by the processor, further cause the biosignal measurement apparatus to detect an abnormality of a P wave or an ST wave, based on the obtained temporal variation of the cardiac potential of the user in the preliminary measurement period, and
determine the start timing and the length of the first period, to cause the P wave or the ST wave having the detected abnormality and the R wave to be included in the second period.

2. The biosignal measurement apparatus according to claim 1,
wherein the executable instructions, when executed by the processor, further cause the biosignal measurement apparatus to determine the start timing of the first period to be when a predetermined time elapses based on the R wave in the obtained first ECG.

3. The biosignal measurement apparatus according to claim 1,
wherein the executable instructions, when executed by the processor, further cause the biosignal measurement apparatus to determine the start timing of the first period to be when a predetermined time elapses from a most recent time at which the R wave appears in the first ECG.

4. The biosignal measurement apparatus according to claim 1, wherein
a current is applied between the plurality of electrodes at the determined start timing, and
the impedance measurement circuit is configured to measure the impedance between the plurality of electrodes in the first period, based on the potential difference between the plurality of electrodes and a magnitude of the applied current.

5. A biosignal measurement method comprising:
measuring a potential difference between a plurality of electrodes placed on a user's chest;
obtaining a first electrocardiogram (ECG) indicating a temporal variation of a cardiac potential of the user, from the measured potential difference;
setting a start timing of a first period for respiratory measurement of the user using the first ECG obtained during the obtaining step, the first period being a period not including an R wave, the start timing of the first period being set based on a time of an R wave in a period of one heartbeat of the user, such that the first period is set in the period not including the R wave;
determining a length of the first period, based on a time interval between two adjacent R waves in the first ECG obtained during the obtaining step;
receiving a first time at which the R wave is detected most recently, and determining the length of the first period to cause the first period to be included between the first time and a time at which the time interval between the two adjacent R waves elapses from the first time;
measuring a second ECG indicating a temporal variation of a cardiac potential of the user, from the potential difference measured in the measuring of the potential difference in a second period which is a period including an R wave and not including the first period;
measuring an impedance between the plurality of electrodes in the first period;
calculating respiratory information related to the respiration measurement of the user, based on a temporal variation of the impedance measured in the measuring of the impedance;
calculating a heart rate of the user based on a time interval between two adjacent R waves in the first ECG obtained during the obtaining step; and
outputting the respiratory information calculated in the calculating of the respiratory information, the heart rate calculated in the calculating of the heart rate, and at least one of the first ECG and the second ECG for the diagnosing of diseases,
wherein the biosignal measurement method further comprises:

determining a start timing and a length of a preliminary measurement period which is a period for continuously measuring the cardiac potential of the user,
obtaining the temporal variation of the cardiac potential of the user in the preliminary measurement period, from the potential difference measured by the potential difference measurement circuit in the preliminary measurement period, and
determining the start timing and the length of the first period, based on the temporal variation of the cardiac potential of the user in the preliminary measurement period, and
wherein the biosignal measurement method further comprises:
detecting an abnormality of a P wave or an ST wave, based on the obtained temporal variation of the cardiac potential of the user in the preliminary measurement period, and
determining the start timing and the length of the first period, to cause the P wave or the ST wave having the detected abnormality and the R wave to be included in the second period.

6. A non-transitory computer-readable recording medium for use in a computer, the recording medium having a computer program recorded thereon for causing the computer to execute the biosignal measurement method according to claim 5.

7. A biosignal measurement apparatus comprising:
a potential difference measurement circuit configured to measure a potential difference between a plurality of electrodes placed on a user's chest;
an impedance measurement circuit configured to measure an impedance between the plurality of electrodes in a first period which is a period not including an R wave;
a processor; and
a non-transitory computer-readable recording medium having stored thereon executable instructions, which when executed by the processor, cause the biosignal measurement apparatus to:
obtain an electrocardiogram (ECG) indicating a temporal variation of a cardiac potential of the user, from the potential difference measured by the potential difference measurement circuit, wherein the obtained ECG includes the ECG being obtained from the potential difference measured by the potential difference measurement circuit in a second period which is a period including the R wave in the ECG and different from the first period, and includes a part in which the first period and the second period alternate;
determine a start timing of the first period, using the obtained ECG;
calculate respiratory information related to respiration of the user, based on a temporal variation of the impedance measured by the impedance measurement circuit;
obtain the temporal variation of the impedance between the plurality of electrodes, by temporally interpolating the impedance in the second period between the impedance measured in the first period preceding the second period and the impedance measured in the first period following the second period;
calculate the respiratory information based on a peak of a low frequency component of the obtained temporal variation of the impedance;
calculate a plurality of respiratory information candidates by performing the temporal interpolation;

calculate a heart rate of the user;
select, from the plurality of respiratory information candidates, a respiratory information candidate indicating a higher respiratory rate when the calculated heart rate is higher; and
output the selected respiratory information candidate as the respiratory information, the calculated heart rate and the obtained ECG for the diagnosing of diseases.

8. A biosignal measurement apparatus comprising:
a potential difference measurement circuit configured to measure a potential difference between a plurality of electrodes placed on a user's chest;
an impedance measurement circuit configured to measure an impedance between the plurality of electrodes in a first period which is a period not including an R wave;
a processor; and
a non-transitory computer-readable recording medium having stored thereon executable instructions, which when executed by the processor, cause the biosignal measurement apparatus to:
obtain an electrocardiogram (ECG) indicating a temporal variation of a cardiac potential of the user, from the potential difference measured by the potential difference measurement circuit, wherein the obtained ECG includes the ECG being obtained from the potential difference measured by the potential difference measurement circuit in a second period which is a period including the R wave in the ECG and different from the first period, and includes a part in which the first period and the second period alternate;
determine a start timing of the first period, using the obtained ECG;
calculate respiratory information related to respiration of the user, based on a temporal variation of the impedance measured by the impedance measurement circuit;
obtain the temporal variation of the impedance between the plurality of electrodes, by temporally interpolating the impedance in the second period between the impedance measured in the first period preceding the second period and the impedance measured in the first period following the second period;
calculate the respiratory information based on a peak of a low frequency component of the obtained temporal variation of the impedance;
calculate a plurality of respiratory information candidates by performing the temporal interpolation;
select, from the plurality of respiratory information candidates, a respiratory information candidate indicating a lower respiratory rate when an amplitude of the temporal variation of the measured impedance is higher; and
output the selected respiratory information candidate as the respiratory information and the obtained ECG for the diagnosing of diseases.

9. A biosignal measurement apparatus comprising:
a potential difference measurement circuit configured to measure a potential difference between a plurality of electrodes placed on a user's chest;
an impedance measurement circuit configured to measure an impedance between the plurality of electrodes in a first period which is a period not including an R wave;
a processor; and
a non-transitory computer-readable recording medium having stored thereon executable instructions, which when executed by the processor, cause the biosignal measurement apparatus to:
obtain an electrocardiogram (ECG) indicating a temporal variation of a cardiac potential of the user, from the potential difference measured by the potential difference measurement circuit;
determine a start timing of the first period, using the obtained ECG;
calculate respiratory information related to respiration of the user, based on a temporal variation of the impedance measured by the impedance measurement circuit;
determine a start timing and a length of a preliminary measurement period which is a period for continuously measuring the cardiac potential of the user;
obtain the temporal variation of the cardiac potential of the user in the preliminary measurement period, from the potential difference measured by the potential difference measurement circuit in the preliminary measurement period;
determine the start timing and a length of the first period, based on the temporal variation of the cardiac potential of the user in the preliminary measurement period;
detect an abnormality of a P wave or an ST wave, based on the obtained temporal variation of the cardiac potential of the user in the preliminary measurement period;
determine the start timing and the length of the first period, to cause the P wave or the ST wave having the detected abnormality and the R wave to be included in a second period; and
output the calculated respiratory information and the obtained ECG for the diagnosing of diseases.

10. The biosignal measurement apparatus according to claim 7, wherein data corresponding to the calculated respiratory information and data corresponding to the calculated heart rate are obtained simultaneously via the plurality of electrodes.

11. A biosignal measurement apparatus comprising:
a potential difference measurement circuit configured to measure a potential difference between a plurality of electrodes placed on a user's chest;
an impedance measurement circuit configured to measure an impedance between the plurality of electrodes in a first period for respiratory measurement of the user, the first period being a period not including an R wave;
a processor; and
a non-transitory computer-readable recording medium having stored thereon executable instructions, which when executed by the processor, cause the biosignal measurement apparatus to:
obtain a first electrocardiogram (ECG) indicating a temporal variation of a cardiac potential of the user, from the potential difference measured by the potential difference measurement circuit;
set a start timing of the first period using the obtained first ECG, the start timing of the first period being set based on a time of an R wave in a period of one heartbeat of the user, such that the first period is set in the period not including the R wave;
determine a length of the first period, based on a time interval between two adjacent R waves in the obtained first ECG;

receive a first time at which the R wave is detected most recently, and determine the length of the first period to cause the first period to be included between the first time and a time at which the time interval between the two adjacent R waves elapses from the first time;

measure a second ECG indicating a temporal variation of a cardiac potential of the user, from the potential difference measured by the potential difference measurement circuit in a second period which is a period including an R wave and not including the first period;

calculate respiratory information related to the respiration measurement of the user, based on a temporal variation of the impedance measured by the impedance measurement circuit;

calculate a heart rate of the user based on a time interval between two adjacent R waves in the obtained first ECG;

output the calculated respiratory information, the calculated heart rate, and at least one of the first ECG and the second ECG for the diagnosing of diseases;

determine a start timing and a length of a preliminary measurement period which is a period for continuously measuring the cardiac potential of the user;

obtain the temporal variation of the cardiac potential of the user in the preliminary measurement period, from the potential difference measured by the potential difference measurement circuit in the preliminary measurement period;

determine the start timing and the length of the first period, based on the temporal variation of the cardiac potential of the user in the preliminary measurement period;

detect an abnormality of a P wave or an ST wave, based on the obtained temporal variation of the cardiac potential of the user in the preliminary measurement period; and determine the start timing and the length of the first period, to cause the P wave or the ST wave having the detected abnormality and the R wave to be included in the second period.

12. A biosignal measurement method comprising:

measuring a potential difference between a plurality of electrodes placed on a user's chest;

obtaining a first electrocardiogram (ECG) indicating a temporal variation of a cardiac potential of the user, from the measured potential difference;

setting a start timing of a first period for respiratory measurement of the user using the first ECG obtained, the first period being a period not including an R wave, the start timing of the first period being set based on a time of an R wave in a period of one heartbeat of the user, such that the first period is set in the period not including the R wave;

determining a length of the first period, based on a time interval between two adjacent R waves in the first ECG obtained;

receiving a first time at which the R wave is detected most recently, and determining the length of the first period to cause the first period to be included between the first time and a time at which the time interval between the two adjacent R waves elapses from the first time;

measuring a second ECG indicating a temporal variation of a cardiac potential of the user, from the potential difference measured in the measuring of the potential difference in a second period which is a period including an R wave and not including the first period;

measuring an impedance between the plurality of electrodes in the first period;

calculating respiratory information related to the respiration measurement of the user, based on a temporal variation of the impedance measured in the measuring of the impedance;

calculating a heart rate of the user based on a time interval between two adjacent R waves in the first ECG obtained;

outputting the respiratory information calculated in the calculating of the respiratory information, the heart rate calculated in the calculating of the heart rate, and at least one of the first ECG and the second ECG for the diagnosing of diseases;

determining a start timing and a length of a preliminary measurement period which is a period for continuously measuring the cardiac potential of the user;

obtaining the temporal variation of the cardiac potential of the user in the preliminary measurement period, from the potential difference measured by the potential difference measurement circuit in the preliminary measurement period;

determining the start timing and the length of the first period, based on the temporal variation of the cardiac potential of the user in the preliminary measurement period;

detecting an abnormality of a P wave or an ST wave, based on the obtained temporal variation of the cardiac potential of the user in the preliminary measurement period; and determining the start timing and the length of the first period, to cause the P wave or the ST wave having the detected abnormality and the R wave to be included in the second period.

* * * * *